(12) United States Patent
Muraoka et al.

(10) Patent No.: US 9,326,745 B2
(45) Date of Patent: May 3, 2016

(54) DYNAMIC DIAGNOSIS SUPPORT INFORMATION GENERATION SYSTEM

(75) Inventors: Shintaro Muraoka, Hachioji (JP); Tetsuo Shimada, Hino (JP); Sho Noji, Tachikawa (JP)

(73) Assignee: KONICA MINOLTA, INC. (JP)

( * ) Notice: Subject to any disclaimer, the term of this patent is extended or adjusted under 35 U.S.C. 154(b) by 0 days.

(21) Appl. No.: 13/293,521

(22) Filed: Nov. 10, 2011

(65) Prior Publication Data
US 2012/0130238 A1    May 24, 2012

(30) Foreign Application Priority Data

Nov. 22, 2010  (JP) .................. 2010-259651

(51) Int. Cl.
*A61B 6/00* (2006.01)
*G06F 19/00* (2011.01)
(Continued)

(52) U.S. Cl.
CPC ............. *A61B 6/5217* (2013.01); *A61B 6/40* (2013.01); *A61B 6/4233* (2013.01); *A61B 6/4266* (2013.01); *A61B 6/4494* (2013.01); *A61B 6/461* (2013.01); *A61B 6/507* (2013.01); *A61B 6/5264* (2013.01); *A61B 6/54* (2013.01); *A61B 6/563* (2013.01); *G06F 19/321* (2013.01);
(Continued)

(58) Field of Classification Search
CPC .... A61B 6/4233; A61B 6/4494; A61B 6/507; A61B 6/5217; A61B 6/5264; A61B 6/563; G06F 19/321; G06F 19/3481; G06T 2207/10116; G06T 2207/30061; G06T 2207/0016; G06T 7/0016; G06T 7/2053

USPC ................ 600/436; 378/10, 62; 382/128, 132
See application file for complete search history.

(56) References Cited

U.S. PATENT DOCUMENTS 4,755,681 A  *  7/1988  Oka et al. ................. 250/370.01
7,639,857 B2    12/2009  Nonaka
(Continued)

FOREIGN PATENT DOCUMENTS

JP    2003-298939 A    10/2003
JP    2009050529 A     3/2009
(Continued)

OTHER PUBLICATIONS

English translation of Muraoka, WO 2009/090894 provided by the AIPN raw machine translation tool.*

(Continued)

*Primary Examiner* — Katherine Fernandez
(74) *Attorney, Agent, or Firm* — Cantor Colburn LLP

(57) ABSTRACT

A dynamic diagnosis support information generation system includes: a radiation generator capable of irradiating a pulsed radiation; a radiation detector which is provided with a plurality of detecting elements arranged in two-dimension, detects the pulsed radiation irradiated from the radiation generator at each of the plurality of detecting elements and generates frame images successively; and an analysis section which calculates and outputs a feature value relating to a dynamic image of a subject based on a plurality of frame images generated by radiographing the subject by using the radiation generator and the radiation detector, wherein the analysis section calculates the feature value relating to the dynamic image of the subject by corresponding pixels to each others representing outputs of a detecting element at a same position in the radiation detector among the plurality of the frame images.

5 Claims, 26 Drawing Sheets

(51) Int. Cl.
*G06T 7/00* (2006.01)
*G06T 7/20* (2006.01)
(52) U.S. Cl.
CPC .......... *G06F19/3481* (2013.01); *G06T 7/0016* (2013.01); *G06T 7/2053* (2013.01); *G06T 2207/10016* (2013.01); *G06T 2207/10116* (2013.01); *G06T 2207/30061* (2013.01)

(56) References Cited

U.S. PATENT DOCUMENTS

| | | | |
|---|---|---|---|
| 7,689,857 | B2 | 3/2010 | Lewis |
| 8,300,912 | B2 * | 10/2012 | Sanada et al. ................. 382/132 |
| 2006/0147897 | A1 * | 7/2006 | Grinvald et al. ................. 435/4 |
| 2009/0097731 | A1 | 4/2009 | Sanada et al. |
| 2010/0061615 | A1 * | 3/2010 | Galant ......................... 382/132 |

FOREIGN PATENT DOCUMENTS

| | | |
|---|---|---|
| JP | 2009-153678 A | 7/2009 |
| WO | 2009090894 A1 | 7/2009 |
| WO | WO 2009/090894 * | 7/2009 |

OTHER PUBLICATIONS

Office Action for the Japanese patent application No. 2010-259651, dated May 27, 2014. English translation attached.
Chinese Second Office Action corresponding to Application No. 201110362826.9; Issue Date: Feb. 9, 2015, with English translation.
English Translation of Claims and Description Muraoka (JP2009090894).
English Translation of Claims and Description Muraoka (JP2009090394).
US Non Final Office Action corresponding to U.S. Appl. No. 14/543,239, Issued Nov. 19, 2015.

* cited by examiner

521

| TUBE TYPE | BUCKY'S ID | FPDID | IMAGE RECEPTION TIME |
|---|---|---|---|
| SINGLE SHOOTING/ CONTINUOUS SHOOTING | 1001 | | |
| | 2001 | | |
| PORTABLE (SINGLE SHOOTING) | — | | |
| — | — | | |

| BLOCK SIZE (mm) | VENTILATION | MAXIMUM AIR FLOW VELOCITY | AMOUNT OF BLOOD | PROCESSING TIME |
|---|---|---|---|---|
| 0.5 | ◎ | ◎ | ◎ | X |
| 1 | ◎ | ◎ | ◎ | △ |
| 2 | ○ | ○ | ○ | △ |
| 5 | △ | △ | △ | ○ |
| 10 | X | X | X | ○ |

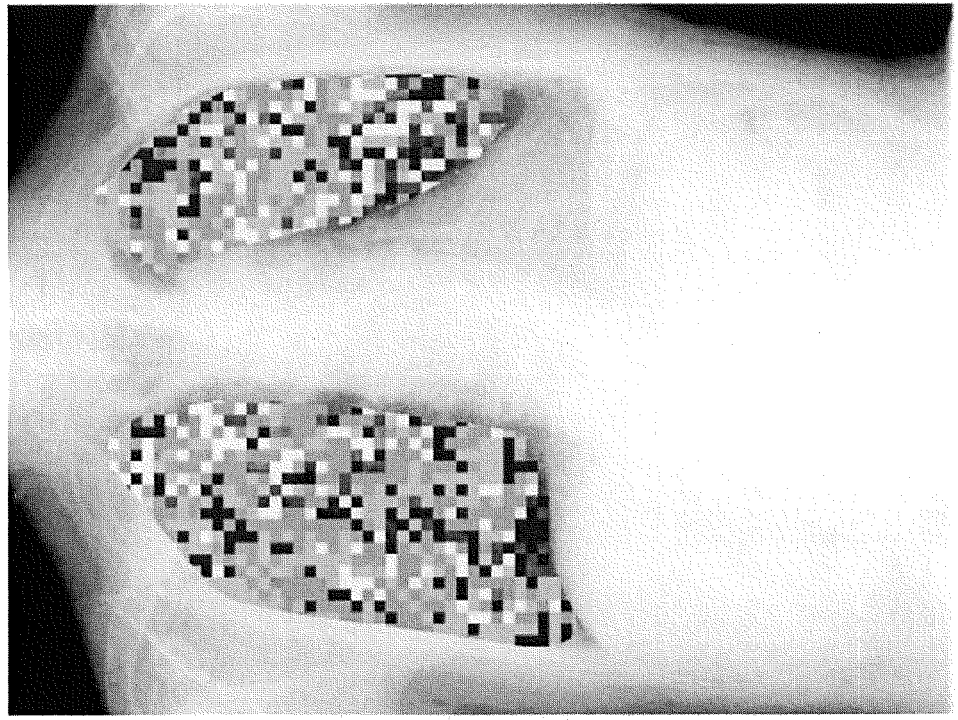
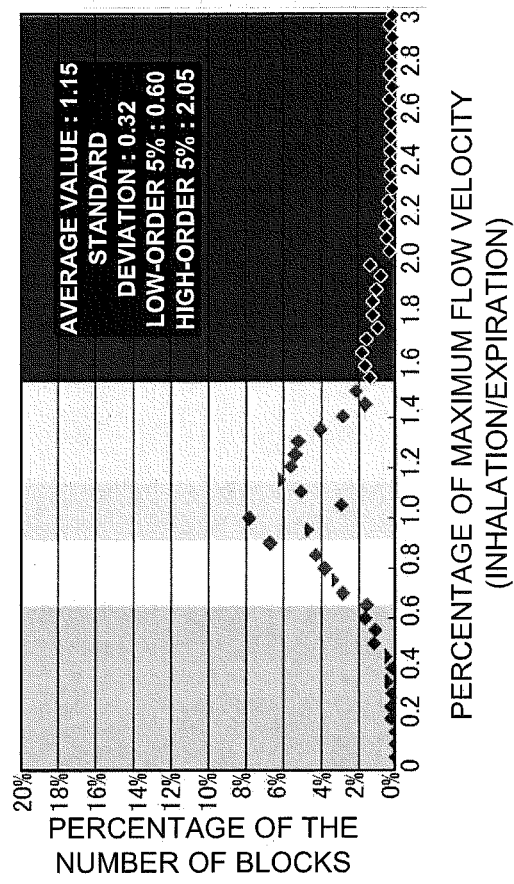
FIG. 11B

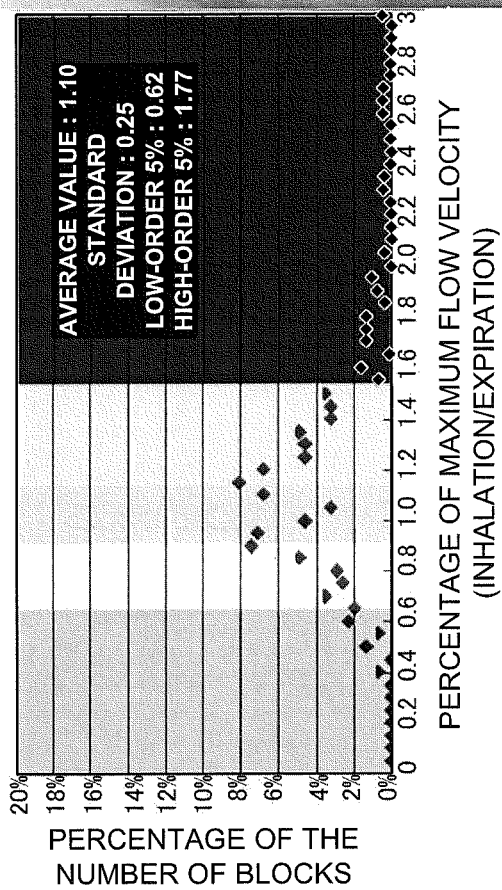
FIG. 11C

FIG. 12A

| FEATURE VALUE | VENTILATION | MAXIMUM FLOW VELOCITY RATIO | VENTILATION DELAY TIME | AMOUNT OF BLOOD FLOW | BLOOD FLOW DELAY TIME | PROCESSING TIME | 1/8 THINNING | PATIENT EXPOSURE TO RADIATION (INCOMING SURFACE DOSAGE IN TEN SECONDS) |
|---|---|---|---|---|---|---|---|---|
| FRAME RATE 2 | | | | | | | | |
| 3.75 | × | × | × | × | × | ◎ | ◎ | ◎ 0.05 mGy |
| 5 | △ | △ | × | × | × | ○ | ◎ | ◎ 0.10 mGy |
| 7.5 | ○ | ○ | × | × | × | ○ | ◎ | ○ 0.14 mGy |
| 10 | ◎ | ◎ | △ | △ | × | △ | ◎ | ○ 0.20 mGy |
| 15 | ◎ | ◎ | ○ | ◎ | × | × | ◎ | ○ 0.27 mGy |
| 30 | ◎ | ◎ | ◎ | ◎ | ○ | × | ○ | △ 0.40 mGy |
|  |  |  |  |  |  |  |  | × 0.80 mGy |

FIG. 12B

| FEATURE VALUE | VENTILATION | MAXIMUM FLOW VELOCITY RATIO | VENTILATION DELAY TIME | AMOUNT OF BLOOD FLOW | S/N PER FRAME |
|---|---|---|---|---|---|
| FRAME RATE 2 | | | | | |
| 3.75 | × | × | × | × | ◎ |
| 5 | △ | △ | × | × | ◎ |
| 7.5 | ○ | ○ | × | × | ○ |
| 10 | ◎ | ◎ | × | △ | ○ |
| 15 | ◎ | ◎ | △ | ○ | ○ |
| 30 | △ | △ | △ | × | △ |
|  |  |  |  |  | × |

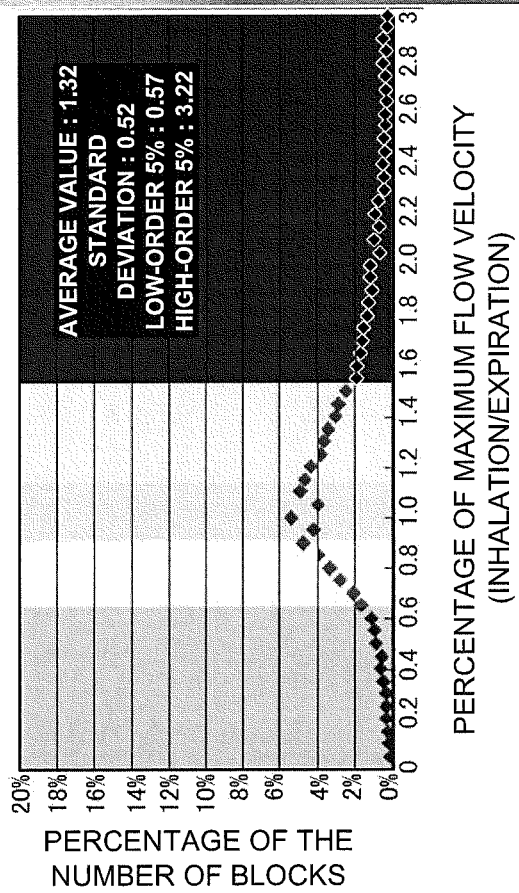
FIG. 13A

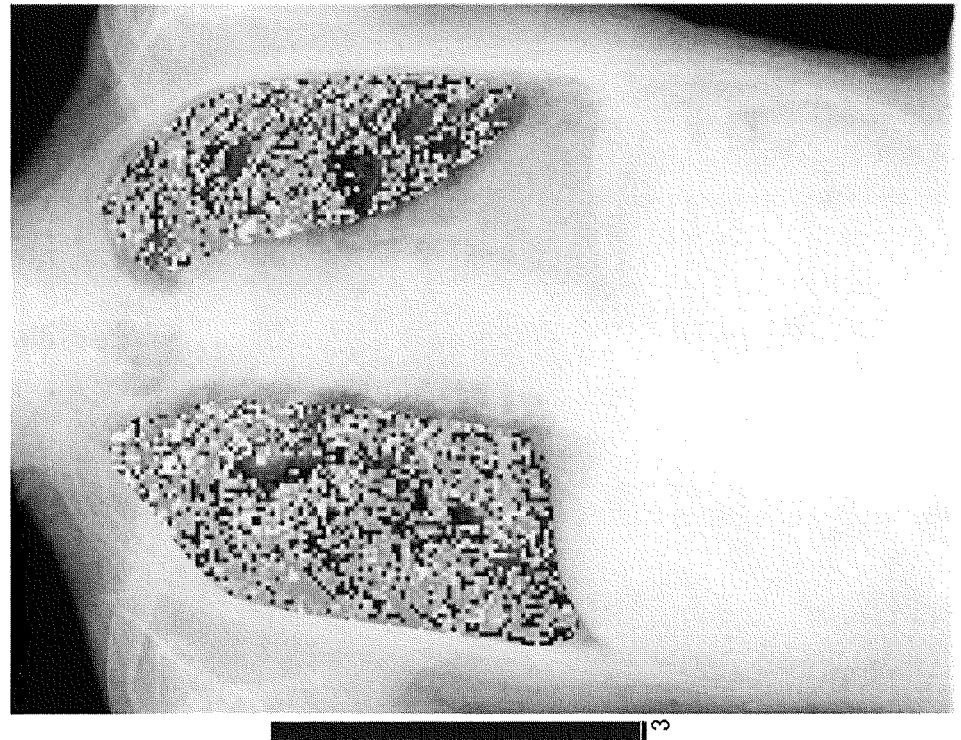
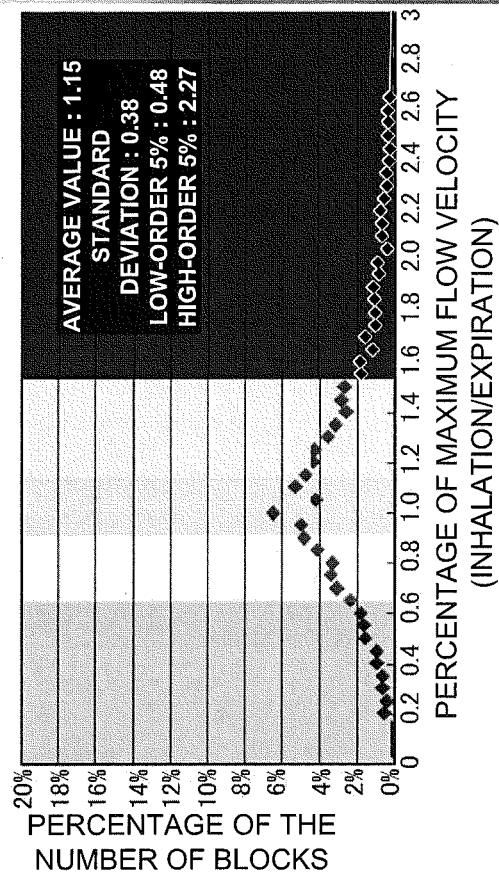
FIG. 13B

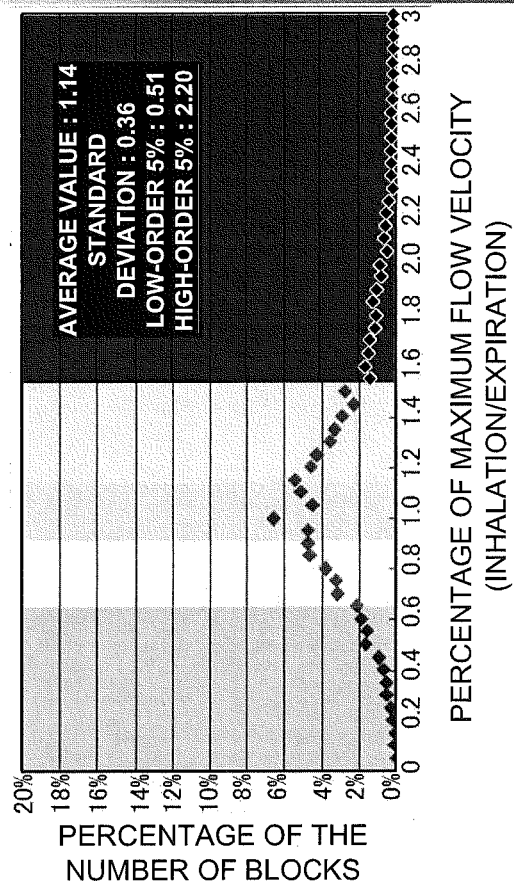
FIG. 13C

FIG. 13D
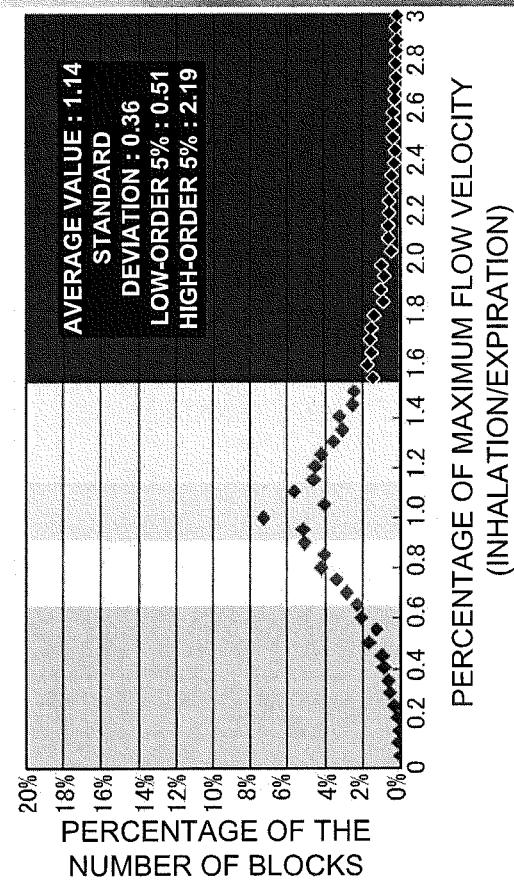

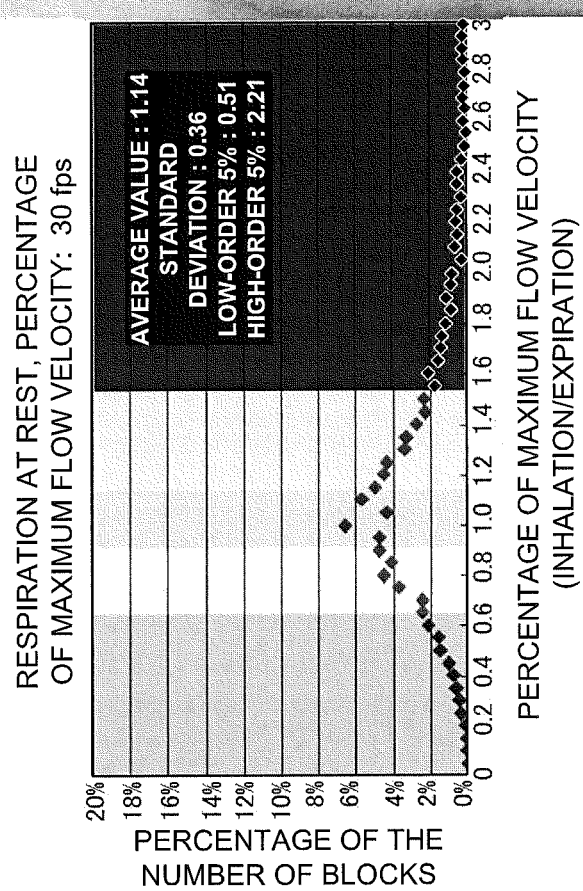
FIG. 13E

FRAME RATE 3.75 fps

FRAME RATE 30 fps

FIG. 15A
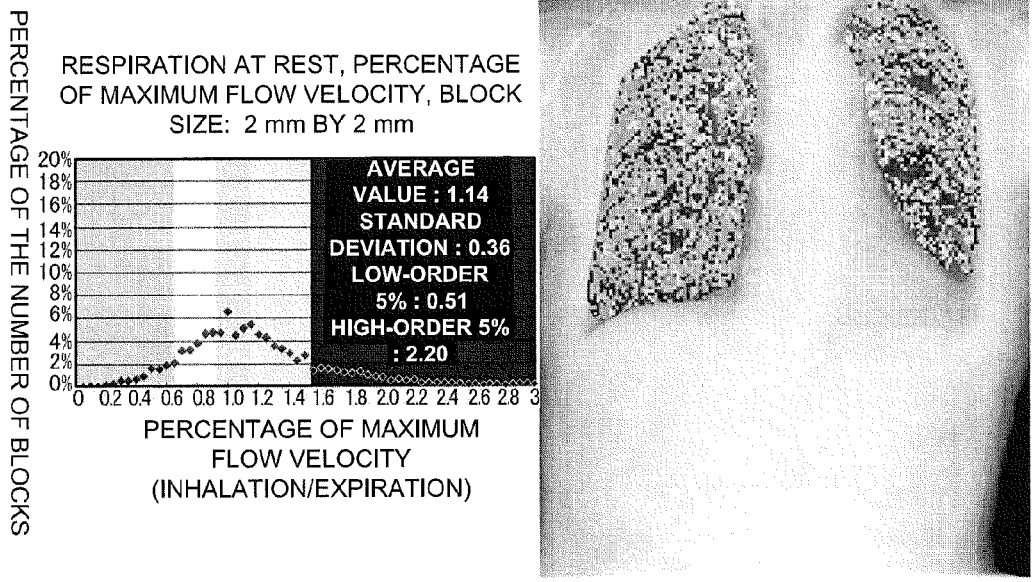
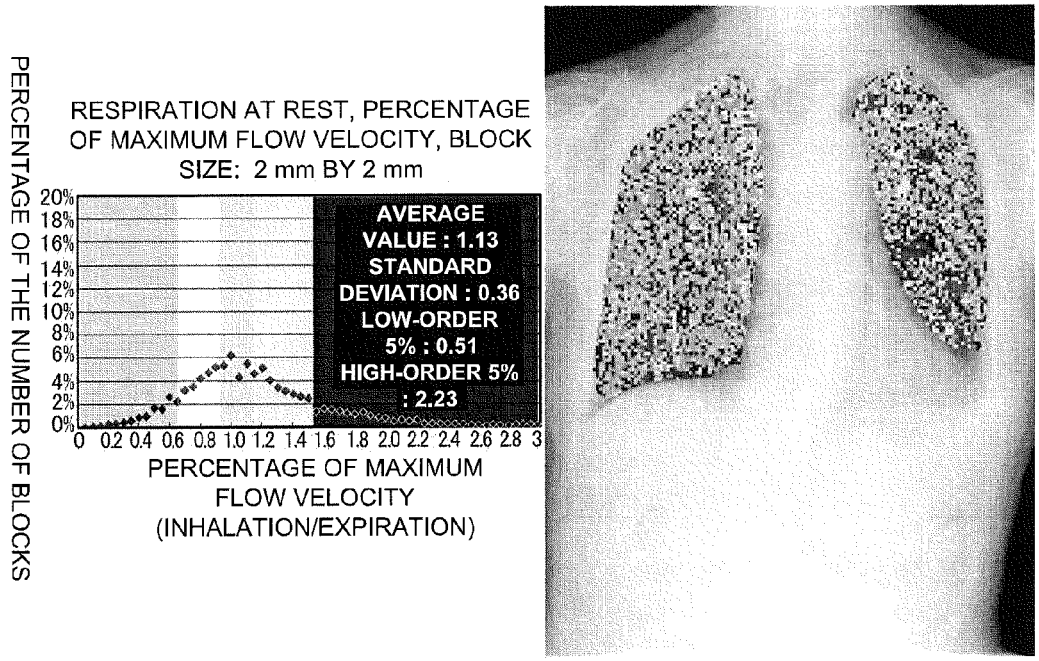

FIG. 15B
BINNING VENTILATION
INTER-FRAME DIFFERENCE IMAGE
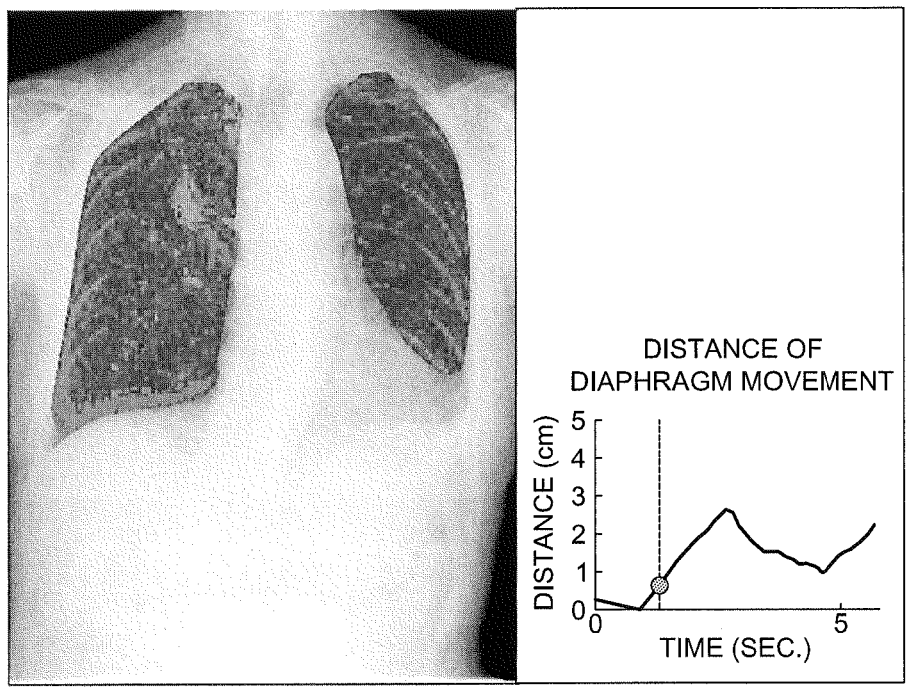
THINNING-OUT VENTILATION
INTER-FRAME DIFFERENCE IMAGE
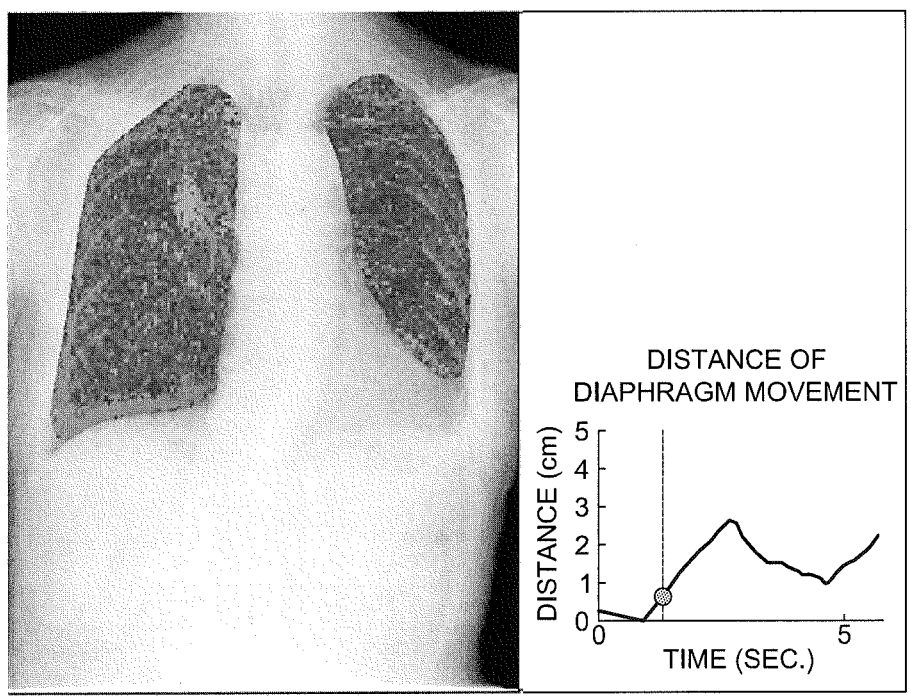

FIG. 15C
BINNING BLOOD FLOW
INTER-FRAME DIFFERENCE IMAGE
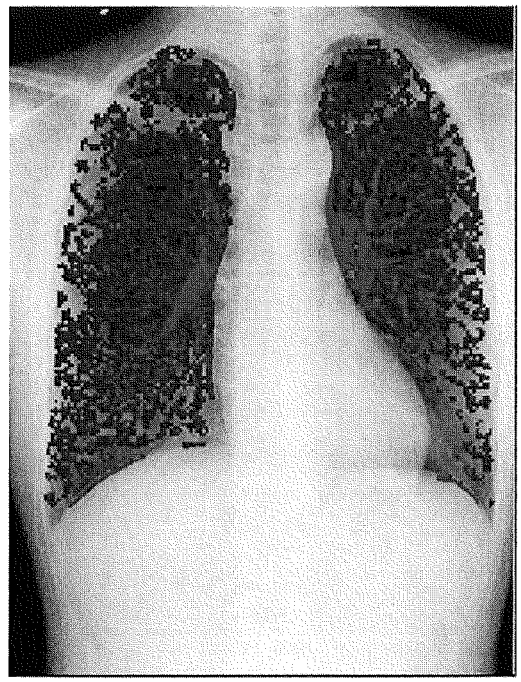
THINNING-OUT BLOOD FLOW
INTER-FRAME DIFFERENCE IMAGE
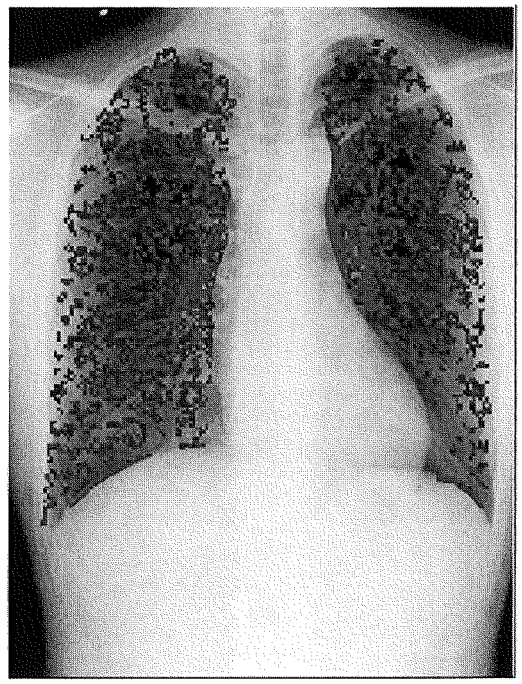

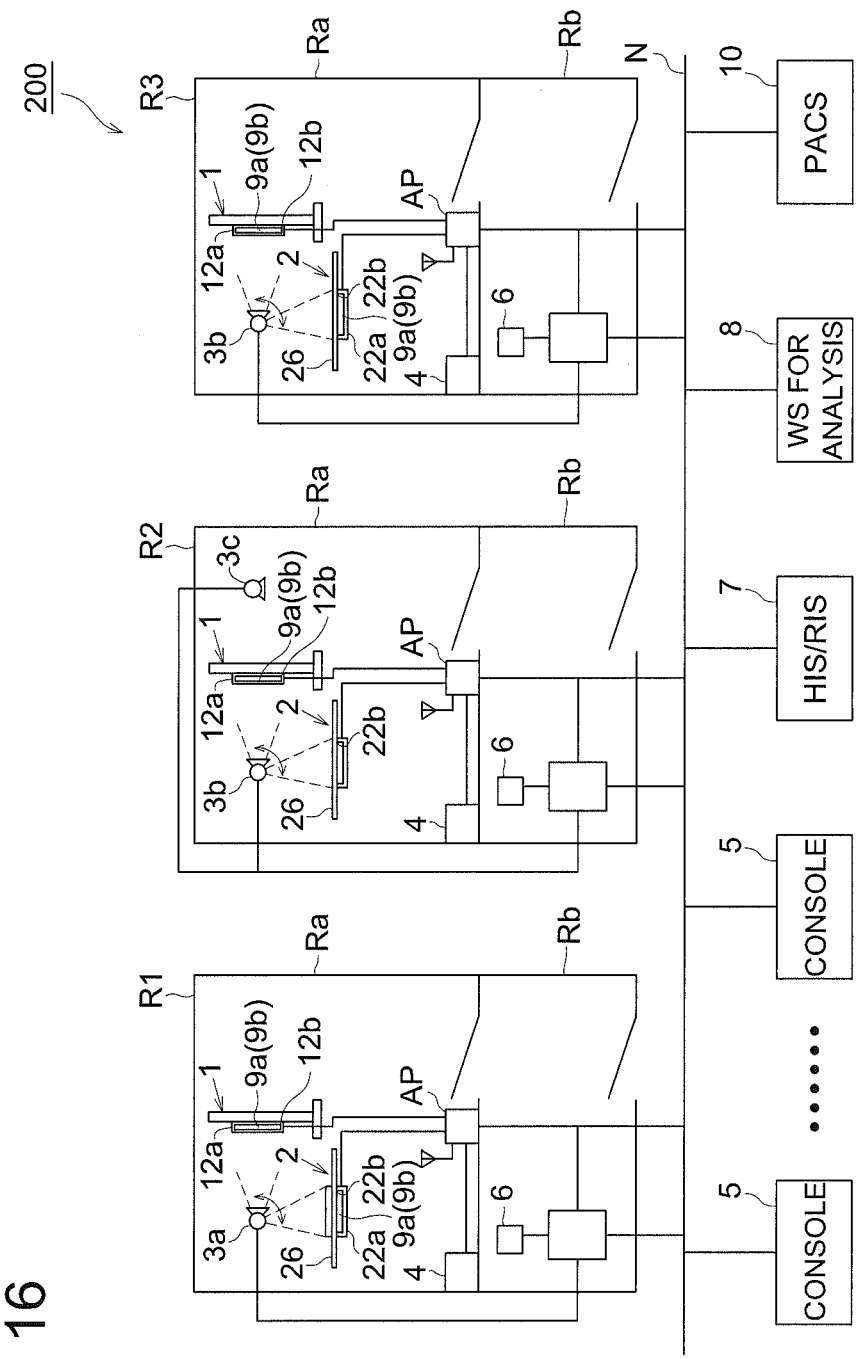

DYNAMIC DIAGNOSIS SUPPORT INFORMATION GENERATION SYSTEM

RELATED APPLICATION

This application is based on Japanese Patent Application NO. 2010-259651 filed on Nov. 22, 2010 in Japanese Patent Office, the entire content of which is hereby incorporated by reference.

FIELD OF THE INVENTION

The present invention relates to a dynamic diagnosis support information generation system.

BACKGROUND OF THE INVENTION

In one of the proposals submitted in recent years, a FPD (Flat Panel Detector) compatible with moving images is used for radiographing dynamic image of a subject, and the feature value of the relevant moving subject is calculated based on a series of frame images captured by radiographing dynamic image. The resulting diagnosis support information is supplied to a doctor to assist earlier diagnosis (e.g., Japanese Unexamined Patent Application Publication No. 2003-298939 and Japanese Unexamined Patent Application Publication No. 2009-153678).

PROBLEMS TO BE SOLVED BY THE INVENTION

The Japanese Unexamined Patent Application Publication No. 2003-298939 and Japanese Unexamined Patent Application Publication No. 2009-153678 relate to the diagnosis support information on the respiratory movement of the chest. When analyzing an item related to feature value for the respiratory movement of the chest such as the amount of ventilation and the amount of blood flow, comparison is made among a plurality of frame images. In order to enhance analysis precision, the position of the structure in the lung field is adjusted among the frame images. Thus, so-called process of warping has been considered as essential in the conventional art.

To perform the process of warping it is necessary to divide one frame image into a plurality of small areas and then extract on a per-frame image basis a small area containing the drawing of the same portion as that of the structure drawn in each of the small areas of this frame image. In the process of warping in general, positioning is performed based on the spatial density change due to the structure in the lung field. This requires the density of the structure to be faithfully (uniformly) reproduced for each frame image. Thus, the fluctuation in the output of each pixel of a detector must be minimized wherever possible (hence, the fluctuation must be corrected by various correction processes such as offset correction, gain correction, correction of defective pixel and lag correction). This requires much correction time. Furthermore, higher-precision warping requires use of an image of finer resolution, hence a detector of smaller pixel size. This results in an increase in the data capacity for each frame image and a substantial increase in the capacity of the entire data to be processed. This requires hardware such as a high-capacity memory and high-speed CPU and longer processing time.

The problem to be solved by the present invention is to reduce the processing time in the analysis of a dynamic image and to calculate the feature value for a moving subject, without requiring use of hardware such as a high-capacity memory and high-speed CPU.

SUMMARY

One aspect of the present invention is a dynamic diagnosis support information generation system comprising a radiation generator capable of irradiating a pulsed radiation; a radiation detector which is provided with a plurality of detecting elements arranged in two-dimension, detects the pulsed radiation irradiated from the radiation generator at each of the plurality of detecting elements and generates frame images successively; and an analysis section which calculates and outputs a feature value relating to a dynamic image of a subject based on a plurality of frame images generated by radiographing the dynamic image of the subject by using the radiation generator and the radiation detector, wherein the analysis section calculates the feature value relating to the dynamic image of the subject by corresponding pixels to each others representing outputs of a detecting element at a same position in the radiation detector among the plurality of the frame images.

BRIEF DESCRIPTION OF THE DRAWINGS

FIG. 11B is a diagram showing the result of analyzing the maximum flow velocity ratio when the block size is 5 mm×5 mm;

FIG. 11C is a diagram showing the result of analyzing the maximum flow velocity ratio when the block size is 10 mm×10 mm;

FIG. 12A is a diagram showing the result of analyzing the representative items in the process of analysis, processing time and result of evaluating the exposure of a patient to radiation, when the frame rate is changed while the exposure dose of each frame image is kept constant;

FIG. 12B is a diagram showing the result of analyzing the representative items in the process of analysis, processing time and result of evaluating the S/N ratio, when the frame rate is changed while the overall exposure dose is kept constant;

FIG. 13A is a diagram showing an example of the result of analyzing the maximum flow velocity ratio, when the block size is 2 mm×2 mm and the frame rate is two frames per second, with the overall exposure dose kept constant;

FIG. 13B is a diagram showing an example of the result of analyzing the maximum flow velocity ratio, when the block size is 2 mm×2 mm and the frame rate is 3.75 frames per second, with the overall exposure dose kept constant;

FIG. 13C is a diagram showing an example of the result of analyzing the maximum flow velocity ratio, when the block size is 2 mm×2 mm and the frame rate is 7.5 frames per second, with the overall exposure dose kept constant;

FIG. 13D is a diagram showing an example of the result of analyzing the maximum flow velocity ratio, when the block size is 2 mm×2 mm and the frame rate is 15 frames per second, with the overall exposure dose kept constant;

FIG. 13E is a diagram showing an example of the result of analyzing the maximum flow velocity ratio, when the block size is 2 mm×2 mm and the frame rate is 30 frames per second, with the overall exposure dose kept constant;

FIG. 15A is a diagram wherein the upper half shows an example of the result of analyzing the maximum flow velocity ratio when binning processing has been applied, on condition that the block size is 2 mm×2 mm and the frame rate is 3.75 frames per second, with the overall exposure dose kept constant;
and the lower half shows an example of the result of analyzing the maximum flow velocity ratio when thinning processing has been applied, on condition that the block size is 2 mm×2 mm and the frame rate is 3.75 frames per second, with the overall exposure dose kept constant;

FIG. 15B is a diagram wherein the upper half shows an example of applying the binning processing to the inter-frame differential image for ventilation, on condition that the block size is 2 min×2 mm; and the lower half shows an example of the result of analyzing the maximum flow velocity ratio when thinning processing has been applied, on condition that the block size is 2 mm×2 mm;

FIG. 15C is a diagram wherein the upper half shows an example of applying the binning processing to the inter-frame differential image for blood flow, on condition that the block size is 2 mm×2 mm; and the lower half shows an example of the result of analyzing the maximum flow velocity ratio when thinning processing has been applied, on condition that the block size is 2 mm×2 mm;

FIG. 16 is a diagram showing an example of a variation of the diagnosis support information generation system;

DESCRIPTION OF EMBODIMENTS

Referring to diagrams, the following describes the embodiments of the diagnosis support information generation system in the present invention, without the present invention being restricted to the examples illustrated below.

Embodiment 1

Figure 1:
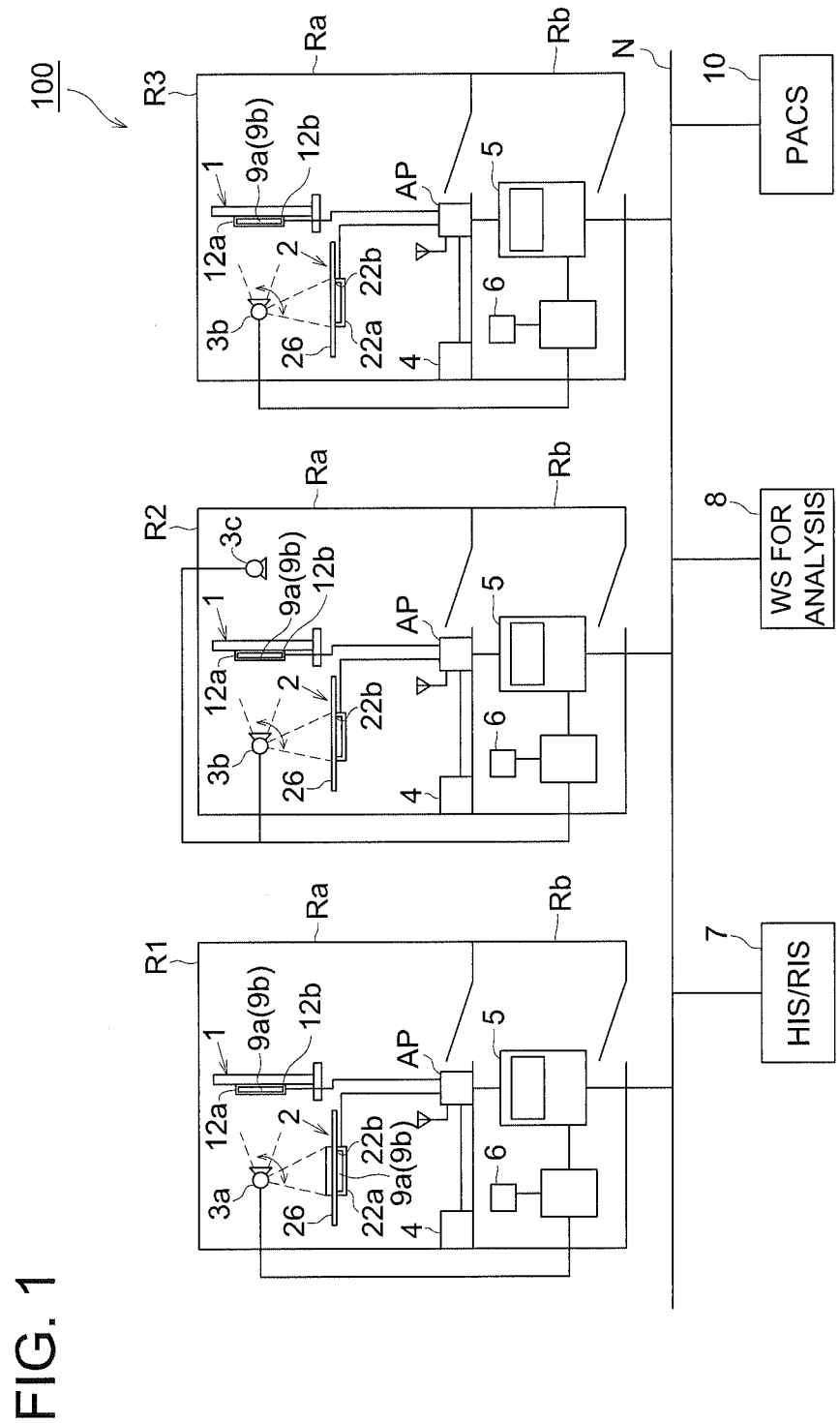
FIG. 1 is a diagram representing the overall structure of a diagnosis support information generation system in the present embodiment.

FIG. 1 is a diagram representing the overall structure of a diagnosis support information generation system 100 in the present embodiment.

The radiographing rooms R1 through R3 of FIG. 1 are used to apply radiation to a subject (i.e., radiographed region of a patient) as part of the patient's body to perform radiographing dynamic image of the subject or to capture a still image of the subject.

Radiographing dynamic image refers to an act of capturing a plurality of images (i.e., continuous radiographing) by a pulse-like application of such a radiation as X-ray to a subject successively. Radiographing dynamic image captures the dynamic and cyclic movement of the subject including the morphological changes of expansion and contraction of the lung resulting from the respiratory movement and beating of the heart. A series of images captured by this continuous radiographic operation are called dynamic images. Further, each of a plurality of images constituting the dynamic image is called a frame image.

The method of capturing a still image is used for diagnosis based on the density resolution of the radiographed region, as in the conventional film method or CR system. This is a method for one irradiation of a subject with radiation such as X-ray to get one still image.

The radiographing room R1 is a room equipped with a radiation source 3a capable of single shooting and continuous shooting and is used for radiographing dynamic image or still image of a subject.

The radiographing room R1 is provided with a Bucky's radiographic device 1 for 3D radiographing, Bucky's radiographic device 2 for a patient at recumbent position, radiation source 3a, cradle 4, console 5, operation console 6 and access point AP, for example.

The radiographing room R2 is provided with a radiation source 3b capable of single shooting alone, and a radiation source 3c for portable photographing, and is used to capture a still image.

The radiographing room R2, Bucky's radiographic device 1 for a patient at standing position, Bucky's radiographic device 2 for a patient at recumbent position, radiation source 3b, 3c, cradle 4, console 5, operation console 6 and access point AP, for example.

The radiographing room R3 is provided with a radiation source 3b, and is used to capture a still image of a subject.

The radiographing room R3 includes a Bucky's radiographic device 1 for a patient at standing position, Bucky's radiographic device 2 for a patient at recumbent position, radiation source 3b, cradle 4, console 5, operation console 6 and access point AP, for example.

Each of the radiographing rooms R1 through R3 is provided with an anteroom Rb and radiographing room Ra. The anteroom Rb contains a console 5 and operation console 6 to protect the operator such as a radiographer against exposure to radiation.

The Bucky's radiographic device 1 is used to hold the FPD 9a or 9b when radiographing a patient at standing position.

Figure 2:
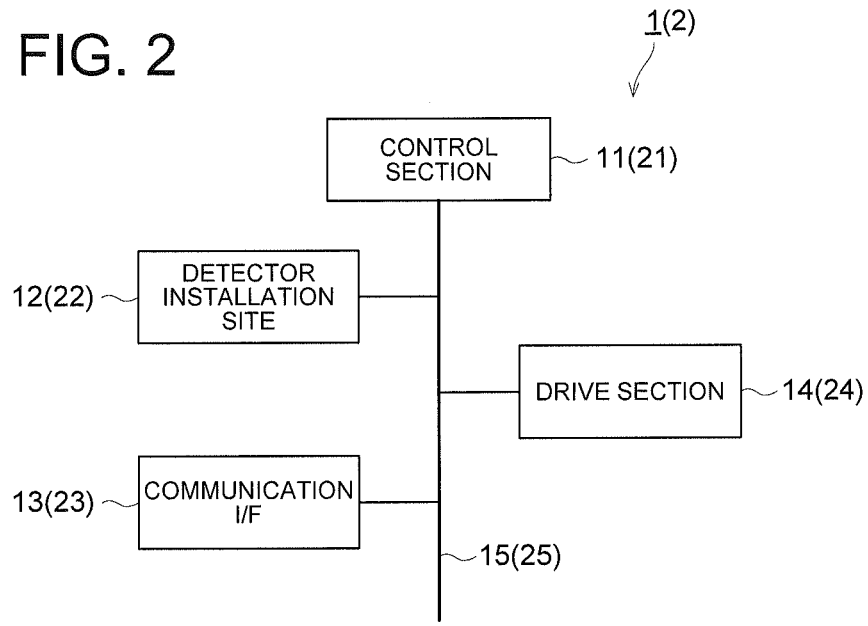
FIG. 2 is a block diagram showing the functional structure of a Bucks radiographic device.

FIG. 2 shows the functional structure of a Bucky's radiographic device 1. As shown in FIG. 2, the Bucky's radiographic device 1 includes a control section 11, detector installation site 12, communication I/F 13 and drive section 14.

The control section 11 includes a CPU (Central Processing Unit), ROM (Read Only Memory) and RAM (Random Access Memory). The ROM of the control section 11 stores various processing programs for controlling various portions of the Bucky's radiographic device 1, data required for processing, Bucky's ID as information for identifying the Bucky's radiographic device 1 and so on. The CPU takes centralized control of various portions of the Bucky's radiographic device 1 in collaboration with the programs stored in the ROM.

For example, when the FPD 9a or 9b has been mounted on the detector installation site 12, the control section 11 sends a request for transmission of the FPD ID (FPD identification information) through the connector 12b mounted on the FPD. When the FPD ID has been received, the Bucky's ID as the identification number of its own is associated with the FPD ID and sent to the console 5 through the communication I/F 13. Also, the received FPD ID is stored in the RAM on the temporary basis.

Further, for example, when the FPD has been removed from the detector installation site 12, the control section 11 sends FPD ID to the console 5 through the communication I/F 13, and requests cancellation of this FPD ID (from the radiographing management table 521).

The detector installation site 12 has a holder 12a for holding the FPD (FPD 9a or FPD 9b) and a connector 12b for linking the connector 94 of the FPD mounted on the holder 12a. The connector 12b is used to exchange data with the FPD mounted on the holder 12a, and to send power to the FPD.

The communication I/F 13 is an interface for exchanging data with the external equipment such as the console 5 via a communication cable through an access point AP.

The drive section 14 moves the detector installation site 12 in the vertical or horizontal direction in response to the operation of the foot switch (not illustrated).

The Bucky's radiographic device 2 holds the FPD 9a or 9b to capture images at the time of radiographing a patient at the recumbent position.

The Bucky's radiographic device 2 is equipped with a control section 21, detector installation site 22, communication I/F 23 and drive section 24. The control section 21, detector installation site 22, communication I/F 23, and drive section 24 have the same structures as those of the aforementioned control section 11, detector installation site 12, communication I/F 13, and drive section 14, and will be not described to avoid duplication. The Bucky's radiographic device 2 is provided with a subject stand 26 on which a subject lies.

The radiation source 3a is a radiation generator capable of single shooting and continuous shooting (irradiation of pulsed radiation). The radiation source 3a is suspended from the ceiling of the radiographing rooms R1 and R3, for example, and is started according to the instruction from the console 5 at the time of radiographing. The radiation source 3a is adjusted to a prescribed position and direction by a drive mechanism (not illustrated). By changing the direction of applying radiation, radiation is applied to the FPD 9a or 9b mounted on the Bucky's radiographic device 1 for standing position or Bucky's radiographic device 2 for recumbent position. Further, according to the instruction from the console 5, the radiation source 3a provides a single or continuous radiographic operation to capture a still image or dynamic images.

The radiation source 3b is a radiation generator capable of single shooting alone. The radiation source 3b is suspended from the ceiling of the radiographing room R2, for example. It is started according to the instruction from the console 5 at the time of radiographing. The radiation source 3b is adjusted to a prescribed position and direction by a drive mechanism (not illustrated). By changing the direction of applying radiation, radiation is applied to the FPD 9a or 9b mounted on the Bucky's radiographic device 1 for standing position or Bucky's radiographic device 2 for recumbent position. Further, according to the instruction from the console 5, the radiation source 3b provides a single radiographic operation to capture a still image.

The radiation source 3c is a portable radiation source. The radiation source 3c is capable of single shooting alone.

The cradle 4 has a connector (not illustrated) to be connected with a mounted FPD. When the FPD is mounted in position, the FPD ID is obtained from the mounted FPD through the connector, and is notified to the console 5.

Upon receipt of the FPD ID, the console 5 places the FPD under its control to control startup and sleep transition.

In the present embodiment, when the FPD is brought into or out of the radiographing room, the cradle 4 is mounted in position. This procedure ensures that entry of the FPD into the radiographing room or its removal can be detected by the console 5 through the cradle 4. The entry of the FPD into the radiographing room or its removal can be achieved by another method. For example, the RFID method disclosed in the Official Gazette WO2008/111355 can be used.

The console 5 controls the radiographing operation through the control of the radiation sources 3a and 3b or FPDs 9a and 9b. The console 5 is connected with the HIS/RIS (Hospital Information System/Radiology Information System) 7, WS 8 for analysis, PACS (Picture Archiving and Communication System) 10 and others through the LAN (Local Area Network). Based on the radiographing order information sent from the HIS/RIS7, a step is taken to determine if the radiographing in that order is possible in the radiographing room associated with the console 5 (installed), and the result of this determination is displayed. If radiographing is possible, the console 5 provides control in such a way as to start up the radiation source and FPD used for radiographing. Radiographing operation is then performed.

Figure 3:
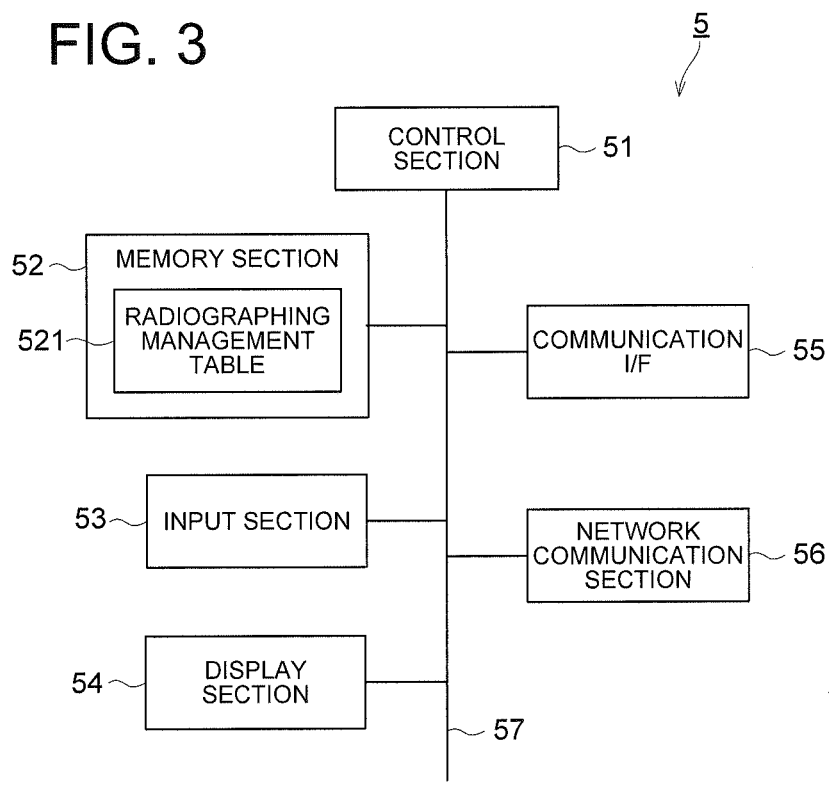
FIG. 3 is a block diagram showing the functional structure of a console.

FIG. 3 shows an example of the major structures of the console 5. As shown in FIG. 3, the console 5 is provided with a control section 51, memory section 52, input section 53, display section 54, communication I/F 55, and network communication section 56. These components are connected by a bus 57.

The control section 51 includes a CPU and RAM. The CPU of the control section 51 reads out the system program stored in the memory section 52 and various programs including processing programs, and expands them in the RAM. Various forms of processing are performed according to these programs.

For example, when the FPD ID and Bucky's ID have been received through the communication I/F 55, the control section 51 writes the FPD ID in the area corresponding to the received Bucky's ID of the radiographing management table 521 (see FIG. 4) of the memory section 52. Also, when the FPD ID has been received from the cradle 4 through the communication I/F 55, the control section 51 writes the FPD ID in the area not associated with the Bucky's ID of the radiographing management table 521 of the memory section 52. Further, when an image data has been received through the Bucky's radiographic device 1 or 2, the control section 51 stores the image reception time in the area corresponding to the Bucky's ID of the Bucky's radiographic device at the source of the radiographing management table 521.

Further, for example, the control section 51 sends inquiries to the HIS/RIS7 through the network communication section 56 at prescribed intervals, and acquires the radiographing order information newly registered by the HIS/RIS7.

Further, for example, the control section 51 performs radiographing/analysis described later. Based on the radiographing order information obtained from the HIS/RIS7, the control section 51 determines whether or not radiographing in this order is possible in the radiographing room containing the console 5 and displays the determination result. If radiographing is possible, the console 5 controls the radiation source used for radiographing and the FPD used for radiographing. Thus radiographing operation is performed.

The memory section 52 includes a HDD (Hard Disk Drive) and semiconductor nonvolatile memory, for example.

The memory section 52 stores various programs and data.

For example, the memory section 52 stores the radiographing management table 521 for managing the radiographing operation in each radiographing room.

Figures 4, 5:
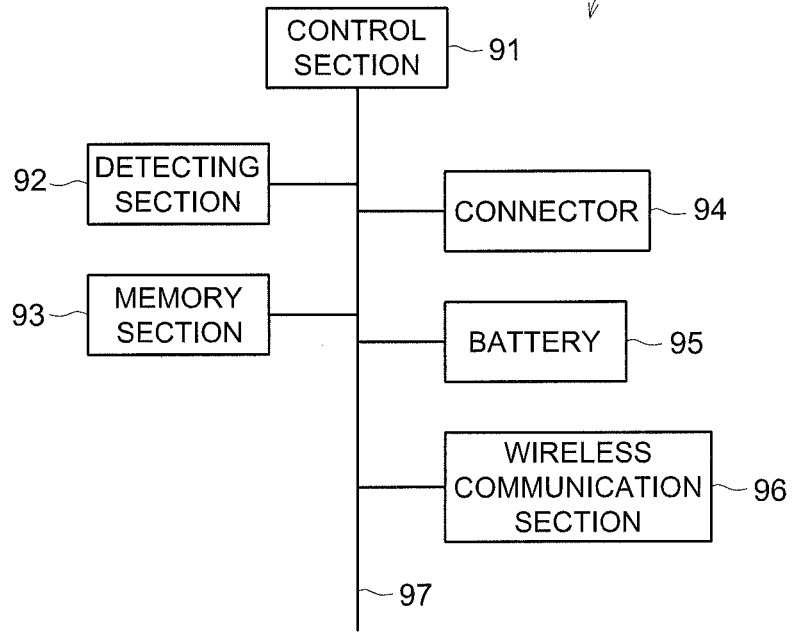
FIG. 4 is a diagram showing an example of data storage in a radiographing management table.
FIG. 5 is a block diagram showing the functional structure of a FPD.

FIG. 4 shows an example of the data stored in the radiographing management table 521. As shown in FIG. 4, the radiographing management table 521 contains such items as a "Bucky's ID", "tube type", "FPD ID", and "image reception time". The "Bucky's ID" and "tube type" areas contain the information on the types of the Bucky's radiographic device and radiation source installed in the radiographing room wherein this console 5 is installed. The "FPD ID" area associated with the Bucky's ID is used to manage the FPD mounted on the Bucky's ID. When the FPD ID and Bucky's ID have been received from the Bucky's radiographic device, the received FPD ID received is stored in the form associated with the Bucky's ID. The "FPD ID" area not associated with the Bucky's ID is used to manage the FPD present in the radiographing room. When the FPD ID has been received from the cradle 4, the received FPD ID is stored. When the FPD has been removed from the Bucky's radiographic device and a FPD ID erasure request has been received, of the FPD ID whose erasure has been requested from the control section 51, the FPD ID stored in the form associated with this Bucky's ID are cancelled. Further, when the FPD ID stored in the "FPD ID" area not associated with the Bucky's ID has been received from the cradle 4, the control section 51 determines that the DPD of that FPD ID has been removed from the radiographing room (i.e., no longer present in the radiographing room) and the FPD ID is erased from the radiographing management table 521. When an image has been received from the communication I/F 55, the time of reception is stored in the "image reception time".

The memory section 52 stores various programs such as the program for image processing, including the processing of gradation and frequency, based on the automatic region recognition for detecting a lesion from an image data. The memory section 52 also stores the image processing parameters for adjusting the radiographed image data to the image quality suited for diagnosis for each region (e.g., lookup table where the gradation curve used in gradation processing is defined, and enhancement of frequency processing).

The memory section 52 stores irradiation conditions and image reading conditions associated with the combination between the type of radiographing (dynamic image or still image) and radiographed region. The irradiation conditions include the pulse rate in the continuous shooting mode, pulse width, pulse interval, number of radiographing frames per shot, X-ray tube current value, X-ray tube voltage value and filter type. The pulse rate can be defined as the number of irradiations per second, and agrees with the frame rate described later. The pulse width is the irradiation time for each operation of irradiation. The pulse interval is the time between the start of the first irradiation to the start of the next irradiation in the continuous shooting mode, and agrees with the frame interval described later. Image reading conditions include the frame rate, frame interval, pixel size and image size (matrix size). The frame rate is defined as the number of frame images to be acquired in one second, and agrees with the pulse rate. In the continuous shooting mode, the frame interval is the time between the start of one frame image acquisition operation and the start of the next frame image acquisition operation, and agrees with the pulse interval.

The memory section 52 stores the FPD IDs of the FPDs 9a and 9b registered in the diagnosis support information generation system 100, and the type of radiographing operations (moving image or still image) permitted by the relevant FPD in the form associated with each other. The memory section 52 also stores the Bucky's ID of the each of the Bucky's radiographic devices 1 and 2 registered in the diagnosis support information generation system 100, and the patient position (standing position or recumbent position) that can be radiographed by the Bucky's radiographic device, in the form associated with each other.

The memory section 52 also stores the radiographing order information sent from the HIS/RIS7 at a prescribed time.

The input section 53 includes a keyboard provided with character entry keys, numeral entry keys and various function keys, and a pointing device such as a mouse. The key depression signal for the key depressed on the keyboard and mouse operation signal as input signals are outputted to the control section 51.

The display section 54 includes such a monitor as a CRT (Cathode Ray Tube) or LCD (Liquid Crystal Display), and shows various forms of screens in conformity to the instruction of the signal inputted from the control section 51.

It is also possible to adopt such a structure that a pressure sensitive type (resistive film pressure type) touch panel (not illustrated) with the transparent electrodes arranged grid-like pattern is formed on the screen of the display section 54, and the touch screen can be made of a display section 54 and input section 53 which are constructed in an integral structure. In this case, the touch panel is designed in such a way that the X-Y coordinates of the power point depressed by the finger or touch pen is detected in terms of a voltage value and the detected position signal is outputted to the control section 51 as an operation signal. The display section 54 can have a higher definition than the monitor used in the PC (Personal Computer) of common use.

The communication I/F 55 is connected through the Bucky's radiographic device 1, Bucky's radiographic device 2, radiation source 3a through 3c, and FPD 9a or 9b and access point AP, and is an interface for data transmission and reception by wired or wireless means. In this embodiment, the communication I/F 55 sends a polling signal to the FPD 9a or 9b through the access point AP as required.

The network communication section 56 is formed of a network interface and others and exchanges data with the external equipment connected to the communication network N through a switching hub.

The operation console 6 is an input device connected to the radiation source in the radiographing room and used to input irradiation instructions.

The HIS/RIS7 generates the radiographing order information in conformity to the registration operation by the operator based on the result of a medical examination by interview with a doctor. The radiographing order information includes patient information such as the full name of a patient as a subject and information on reservation of radiographing such as radiographed region, direction of radiographing, patient position (standing position or recumbent position), method of radiographing, necessity of analysis, and analysis items. The radiographing order information can include other information without being restricted to the aforementioned examples, or can be some of the aforementioned examples.

The WS 8 for analysis is a workstation composed of a control section made of a CPU, RAM and others, a memory section for storing the analysis program, an input section, a display section and a communication section for exchanging data with the external equipment such as a console 5 via the communication network N. In collaboration with analysis programs stored in the control section and memory section, the WS 8 for analysis performs analysis based on a series of frame images sent from the console 5. The result of analysis is sent to the console 5.

The FPD 9a is a radiation detector capable of pulse-radiographing of both dynamic and still images.

FIG. 5 shows an example of the functional structure of an FPD 9a. As shown in FIG. 5, the FPD 9a includes a control section 91, detecting section 92, memory section 93, connector 94, battery 95, and wireless communication section 96. These components are linked by a bus 97.

The control section 91 is composed of a CPU, RAM and others. The CPU of the control section 91 reads various programs such as the system programs and processing programs stored in the memory section 93 and expands them in the RAM. Processing is executed in conformity to the expanded programs.

For example, in response to the request from the Becky's radiographic device 1 or 2 linked through the connector 94, the control section 91 reads the FPD ID as identification information of the FPD 9a from and memory section 93, and sends it to the Bucks radiographic device which has requested reading.

Further, in response to the image reading conditions entered from the console 5, the control section 91 controls the switching section of the detecting section 92, and switches the readings of the electric signals stored in each radiation detecting element (hereinafter referred to as "detecting element"). By the electric signal stored in the detecting section 92, the control section 91 generates image data (still image or frame image). The control section 91 sequentially sends the generated image data to the console 5 through the connector 94 and Bucks radiographic device 1 or 2. It is also possible to make such arrangements that the frame images acquired by radiographing is once stored in the memory section 93 of the FPD 9a and, upon completion of entire radiographing, these frame images are collectively outputted to the console 5 from the FPD 9a.

When the FPD 9a is used as a single body without being mounted on the Bucky's device, the FPD 9a is driven by a battery to perform wireless communication. However, in the radiographing dynamic image mode, it is preferred to change the structure in such a way that the external power is supplied through the Bucky's device and wired communication is performed, as disclosed in the Official Gazette of Japanese Patent Laid-Open No. 4,561,730. This is intended to protect the radiographing (reading) of other frame images from being affected by the noise during transmission of one frame image, because of a drastic increase in the data transfer capacity and transfer time, as compared with the still image radiographing mode. This is also intended to reduce the transfer time and to prevent the battery from being exhausted during a series of radiographic operations.

The detecting section 92 has a glass substrate, for example. Radiation from any one of the radiation sources 3a through 3c is applied to a prescribed position on the substrate. A plurality of detecting elements are arranged in a two-dimensional array, wherein these detecting elements detect the radiation having passed through at least the subject in conformity to the intensity and stores the detected radiation converted into the electric signal. The detecting element is formed of a semiconductor image sensor such as a photodiode. Each of the detecting elements is connected to the switching section of the TFT (Thin Film Transistor) for example, and storing and reading of the electric signal is controlled by the switching section.

Each of the pixels constituting the generated still image or frame image indicates the signal value (called a density value in this document) output from each of the detecting elements of the detecting section 92.

The memory section 93 is formed of a nonvolatile memory of semiconductor, for example. The memory section 93 stores various programs for controlling the detecting section 92, the FPD ID as the identification information of its own, and other information. Further, the memory section 93 temporarily stores the image data outputted from the detecting section 92.

The connector 94 is connected with the connectors on the side of the Bucky's radiographic devices 1 and 2, and exchanges data with the Bucky's radiographic device 1 or 2. The power supplied from the connector of the Bucky's radiographic device 1 or 2 to each functional parts by the connector 94. It is also possible to make such arrangements that the battery 95 is rechargeable.

The battery 95 supplies power to various parts of the FPD 9a under the control of the control section 91. As a battery 95, a freely rechargeable battery, such as a NiCad battery, nickel hydrogen battery or lithium ion battery, can be used.

Similarly to the case of the FPD 9a, the FPD 9b is provided with a control section 91, detecting section 92, memory section 93, connector 94, and battery 95, but the frame rate cannot be set. To be more specific, the FPD 9b is capable of radiographing of still images alone.

The FPD 9b can be used not only as a single body, but also as a detector mounted on the Bucky's radiographic device. When the FPD 9b is mounted on the Bucky's radiographic device, the FPD 9b can be switched from the battery/wireless system over to the wired/power supply system by means of a connector. Thus, even when a plurality of patients are to be shot in the still image mode on a continuous basis, there is no need of worrying about the battery being exhausted.

The PACS10 is equipped with a server device for saving image data and a terminal for radiographic interpretation which acquires a diagnostic image from the relevant server device and displays it. The server device of the PACS10 stores the image data from the console 5 and the data as the result of analysis in the form associated with the radiographing order information.

The following describes the radiographing operation of the diagnosis support information generation system 100.

Figure 6:
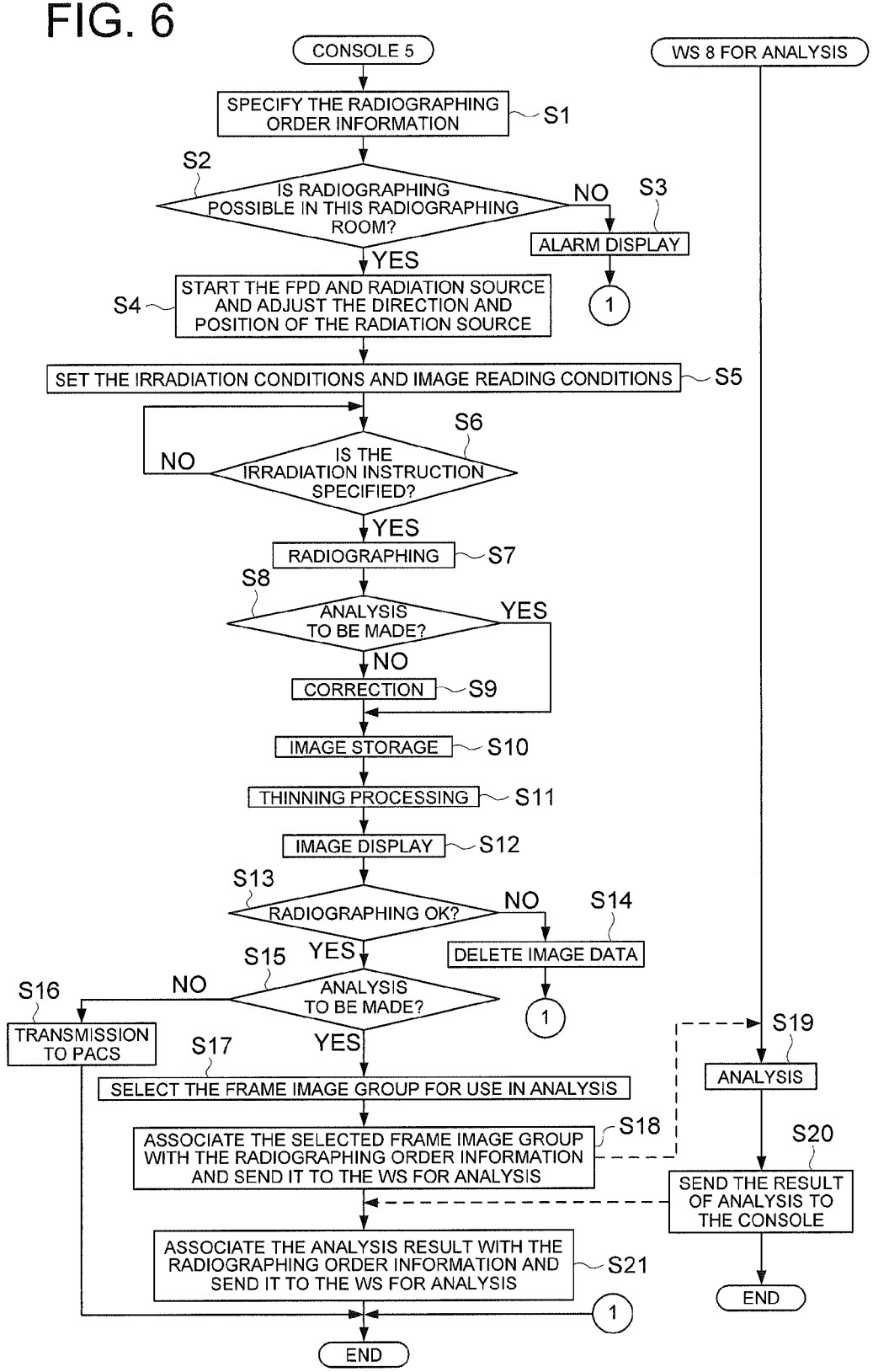
FIG. 6 is a flowchart showing the operation of a diagnosis support information generation system in the first embodiment.

FIG. 6 shows the flow of radiographing and analysis processing performed in the diagnosis support information generation system 100. Processing on the side of the console 5 in FIG. 6 is performed in collaboration with the programs stored in the control section 51 and memory section 52 of the console 5. Processing on the side of the WS 8 for analysis is performed in collaboration with the analysis programs stored in the control section and the memory section of the WS 8 for analysis.

In the first place, the operator of the radiographer operates the input section 53 of the console 5 of any one of the radiographing rooms so that the radiographing order list screen showing the list of radiographing order information will be displayed on the display section 54. The operator then operates the input section 53 to specify from the radiographing order list screen the radiographing order information on the subject to be radiographed.

On the console 5, when the radiographing order information of the subject to be radiographed has been specified from the input section 53 (Step S1), reference is made to the radiographing management table 521 of the memory section 52, and a step is taken to determine if it is possible to perform radiographic operations based on the radiographing order information selected in the radiographing room wherein the relevant console 5 is installed (Step S2). For example, when the radiographing dynamic image has been specified by the radiographing order information, reference is made to the radiographing management table 521. Then, if the radiographing room contains a tube type radiation source capable of continuous shooting and a FPD compatible with radiographing dynamic image, and if that FPD is not being used (when a prescribed time has lapsed since the image reception time), then radiographing dynamic image is determined as possible.

When radiographing according to the selected radiographing order information is determined as possible (Step S2: Yes) in the radiographing room wherein the relevant console 5 is installed, the processing goes to Step S4.

If radiographing according to the selected radiographing order information is determined to be impossible in this radiographing room (Step S2: No), an alarm is indicated on the display section 54 (Step S3). For example, if the tube compatible with continuous shooting is determined to be absent in the radiographing room although radiographing dynamic image has been specified by the radiographing order information (as in the radiographing room R2 of FIG. 1), an alarm message is displayed to notify that radiographing is disabled in this radiographing room. For example, if the FPD 9a compatible with radiographing dynamic image is determined to be absent on the Bucky's radiographic device at the time of starting radiographing dynamic image of the patient position specified by the radiographing order information, an alarm message is displayed prompting the user to mount the FPD 9a on the Bucky's radiographic device for standing position (recumbent position). Then the radiographing/analysis processing terminates. When the FPD 9a compatible with radiographing dynamic image is not mounted on the Bucky's radiographic device at the time of radiographing dynamic image of the patient position specified by the radiographing order information, the contents of the radiographing management table 521 are updated by mounting an FPD compatible with radiographing dynamic image on the relevant Bucky's radiographic device. Thus, radiographing is determined to be possible and processing goes to Step S4.

In this case, it is also possible to make such arrangements that the operator enters the radiographing room to replace the FPD and comes back to the console. Then the processing can be started from Step S1 to ensure reliability.

In Step S4, the radiation source and FPD enabled for radiographing of the specified radiographing order information are started, and the direction and position of the radiation source is adjusted in conformity to the Bucky's radiographic device to be used. If the positions of the FPD and Bucky's radiographic device have been adjusted by the radiographer in conformity to the subject, the direction and position of the radiation source are adjusted accordingly (Step S4). The region and the irradiation conditions and image reading conditions conforming to the mode of radiographing (dynamic or static) are read from the memory section 52, and irradiation conditions are set on the radiation source. At the same time, image reading conditions are set in the FPD through the Bucky's radiographic device (Step S5). If the result of radiographing dynamic image is used for analysis, the frame rate is set to 3.75 frames or more per second to ensure the precision of accuracy in analysis used for diagnosis. In the case of radiographing dynamic image of the lung field, the operator requests the test subject to be relaxed to promote eupnea. If preparation has been made for radiographing, the radiographer moves to the anteroom and operates the operation console 6 to enter the irradiation instruction.

When the irradiation instruction has been entered from the operation console 6 (Step S6: Yes), the radiation source and FPD to be used for radiographing are placed under control, and radiographing operation is performed (Step S7).

In the radiographing dynamic image mode, radiation is applied at pulse intervals preset in Step S5 by the radiation source 3a. A frame image is captured by the FPD 9a at the frame rate preset in Step S5. If the preset number of frame images has been radiographed, a radiographing termination instruction is sent to the radiation source 3a and FPD 9a by the control section 51. The radiographing operation now terminates. The number of frame images to be radiographed indicates the number permitting at least one cycle of radiographing dynamic image. The frame images captured by radiographing are sequentially sent to the console 5 from the FPD 9a through the Bucky's radiographic device.

If analysis is not specified in the radiographing order information, a dark image for offset correction may be read and inputted into the console 5.

In the static radiographing mode, one still image of the subject and one or more dark images for offset correction are captured under the conditions preset in Step S5. The still image and dark image captured by radiographing are sent from the FPD to the console 5 through the Bucky's radiographic device.

A step is taken to determine whether or not to make an analysis using the WS 8 for analysis (Step S8). The decision on whether or not to make an analysis using the WS 8 for analysis is made, for example, in conformity to the radiographing order information specified in Step S1. If radiographing of a still image has been ordered in the radiographing order information, analysis is determined not to be made. If radiographing dynamic image has been ordered and if this order contains the information that analysis is necessary in conformity to the radiographing order information, then analysis is determined to be necessary.

If it is determined that analysis is not made by the WS 8 for analysis (Step S8: No), the image captured by radiographing is corrected (Step S9), and the processing goes to Step S10. In the processing of correction in Step S9, corrections are performed as required, such as offset correction using the aforementioned dark image, gain correction, defective pixel correction, and lag (residual image) correction. When analysis is performed, these corrections can be omitted in order to give priority to reduction of the processing time. In this case, processing goes to Step S10.

In the dynamic analysis, the absolute output of individual pixels in such a case as still images is not very important, and calculation of the feature value based on the inter-frame relative output value (fluctuation component) in individual pixels serves a basis for calculation. Thus, the inventors of the present invention has found out that, even if a part or whole of the aforementioned correction processing has been omitted, it is possible to get nearly the same analysis result as when that collection processing is performed. Accordingly, to reduce the time to get the result of analysis, part or whole of the correction can be omitted.

In Step S10, the frame image or still image captured by radiographing is stored in the memory section 52 in the form associated with the radiographing order information (Step S10). The frame images captured by radiographing are assigned radiographing sequence numbers, and are stored in the header information of each image.

The images entered sequentially are subjected to thinning processing, and are displayed on the display section 54 (Step S11). The term "thinning processing" in the sense in which it is used here refers to the process of reducing the number of pixels in each frame image and still image. For example, the thinning processing includes the processing of creating a thinned-out image made up of pixels at a prescribed pixel interval (hereinafter referred to as "simple thinning processing") and the binning processing wherein the frame image is divided into small areas in units of pixel blocks having a prescribed size (for example, in units of a square of 2 mm×2 mm) to calculate the representative value (hereinafter referred to as "average signal value") for the signal values of the pixels in each small area, and the signal value for pixels in the small area is replaced by the representative value having been calculated. In the binning processing, for dynamic images, the number of pixels of the subject to be observed can be reduced by handling the unit of each small area as one pixel. In the binning processing, division is accomplished in such a way that the small areas corresponding among frame images will be composed of the pixel groups denoting the output at the same position of the detecting element. For example, division is accomplished in units of a square of 2 mm×2 mm wherein the same pixel position (0, 0) on the frame image is used as an origin. It should be noted that each pixel block in the binning processing preferably has the size in conformity to the radiographed region that will be an object of diagnosis (i.e., object to be analyzed). When analysis is to be performed in the later stage, the size preferably conforms to the feature value to be calculated by analysis.

The thinned-out frame image is displayed on the display section 54 (Step S12). The radiographer checks the positioning and other factors by means of the displayed dynamic image, and checks if an image suited to the diagnosis has been captured by radiographing (radiographing: OK) or re-radiographing is necessary (radiographing: NG). The radiographer operates the input section 53 and enters the result of decision. It is also possible to make such arrangements that the frame images captured by radiographing are once stored in the memory section 93 of the FPD 9a, then are collectively sent from the FPD 9a to the console 5 after termination of all the radiographing operations.

If the decision result of "radiographing: NG" has been inputted by the operation of the input section 53 (Step S13: No), a series of frame images stored in the memory section 52 are deleted (Step S14), and this processing terminates. In this case, radiographing is performed again.

If the decision result of "radiographing: OK" has been inputted by the operation of the input section 53 (Step S13: Yes), a step is taken to determine whether or not analysis is performed (Step S15). The decision on whether or not analysis is performed is made in the same way as described in Step S8, for example. If decision is made not to perform analysis (Step S15: No), the radiographed still image or frame image is processed as required, and is sent to the server device of the PACS10 through the network communication section 56 (Step S16). In the server device of the PACS10, the still images or frame images having been received are stored in the form associated with radiographing order information.

If decision is made t to perform analysis (Step S15: Yes), a step is taken to select a group of the frame images to be used or analysis out of the groups of a series of frame images captured by radiographing (Step S17).

Figure 7:
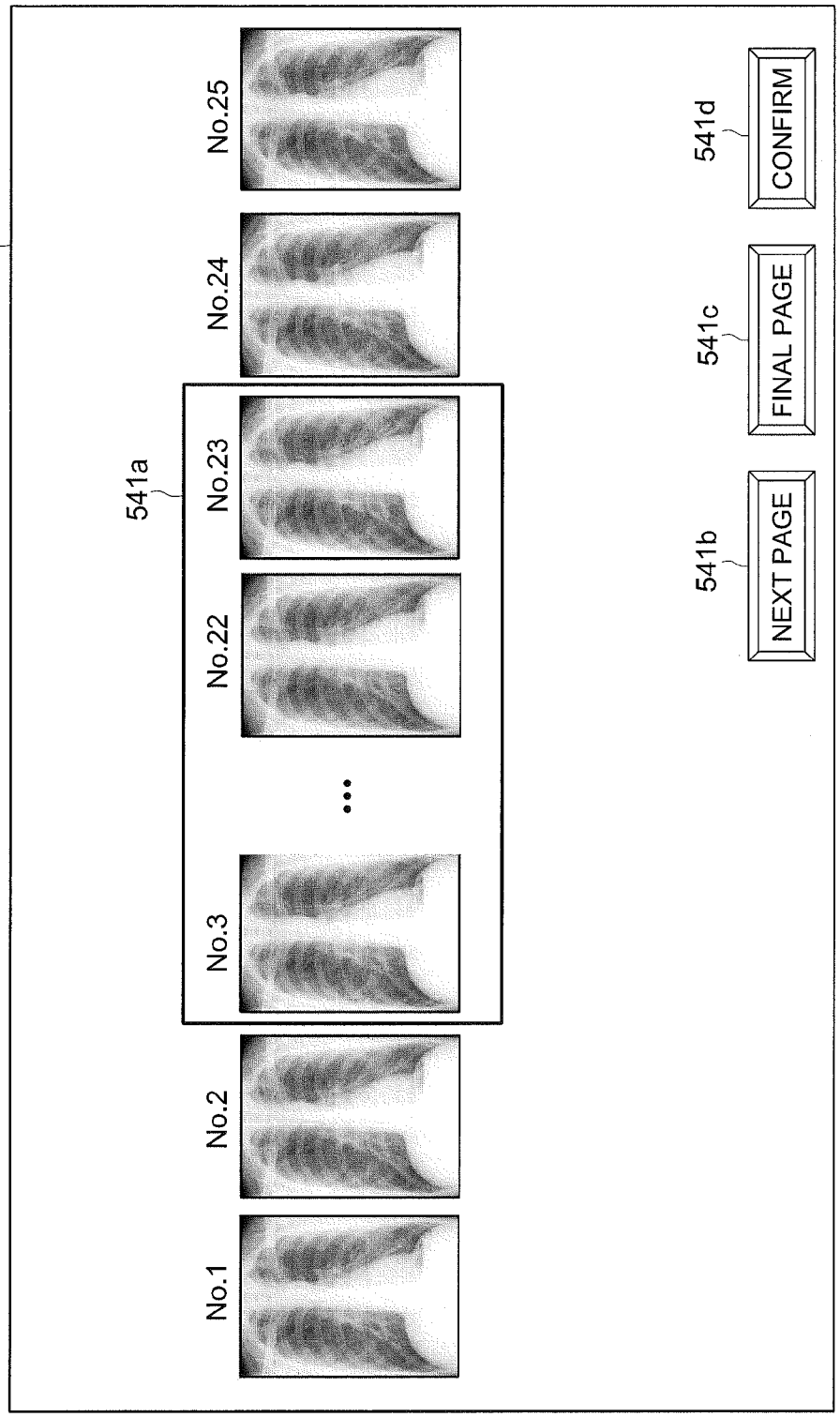
FIG. 7 is a diagram showing an example of the screen for selection.

The following describes the processing in Step S17: In Step S17, the display section 54 shows the selection screen 541 wherein the thumb nail images out of a series of frame images captured by radiographing are arranged in the order of radiographing. FIG. 7 shows an example of the selection screen 541. As shown in FIG. 7, the selection screen 541 displays a series of frame images arranged side by side. Further, the selection frame 541a is also displayed.

If analysis is made using the number of the frame images greater than the number necessary for the analysis, much data transfer time and analysis processing time will be required. This is not recommended. To minimize the processing time, the number of frame images to be used for the analysis must be selected out of a series of frame images radiographed. In the meantime, dynamic images are analyzed mainly based on dynamic cycles or the difference of signal values between adjacent frame images, as will be described later. To ensure that the result of the dynamic image analysis will be the result representing the true feature value of a subject, it is necessary to get a series of continuous frame images in the number greater than one dynamic cycle of the subject. Step S17 provides a selection screen 541 as a GUI that allows the operator to properly select as many continuous frame images as the number required for analysis. To put it more specifically, use of the selection frame 541a for selection prevents selection of images for each discontinuous frame or selection of less than one cycle.

To display the selection frame 541a, the number "n" of images required for analysis is calculated. For example, the dynamic cycle for an average adult is stored in the memory section 52 for each region, and the number "n" of images required for analysis is calculated based on the frame rate included in the mage reading conditions used for radiographing and the dynamic cycle of the subject region. For example, if the ventilation of the lung is to be analyzed, the breathing cycle is about 3.3 seconds for the average adult. Thus, about 20 images are necessary if the frame rate is five (images) per second, and about 30 images are necessary if the frame rate is 7.5 (images) per second. If the number "n" of images required for analysis has been calculated, there will appear a selection frame 541a for enclosing the thumb nail images of the continuous n-frame images. By default, the images having the sequence of radiographing from the first to n-th ordinal positions are shown enclosed by the selection frame 541a. The selection screen 541 is provided with a next-page button 541a, last page button 541c and confirm button 541d. If the next-page button 541a has been depressed, the next page is displayed. When the last page button 541c has been depressed, the last page appears. If one thumb nail image has been selected by the operator, the selection frame 541a is displayed enclosing n-images with the selected frame image being the leading one. If the confirm button 541d has been depressed, the group of the frame images for the thumb nail images enclosed by the selection frame 541a is selected as images used for analysis.

In some cases, it is impossible to get the required number of images if the selected frame image is located at the leading position. In such cases, an alarm pops up on the selection screen 541. It is also possible to make such arrangements that choice is given to the user as to whether analysis is conducted on this pop-up screen with the number of frame images left insufficient or whether images are re-selected. In the present embodiment, the frame image as a starting point to be sued for analysis is left to the choice of the user. It is also possible to make such arrangements that choice of the final image is left to the user.

Depending on the items to be analyzed, it may be necessary to get not only a series of frame images in excess of the continuous dynamic cycle but also, for the lung field, the images of the maximum expiration and the maximum inhalation, for example. In such cases, in addition to selection by the selection frame 541a, section of a frame image is enabled by one-shot operation. For example, by clicking on the thumb nail image of the frame image using the mouse of the input section 53, the selection frame 541a is moved so that the image will be the starting point. The frame image is selected by one-shop operation by double-clicking on the thumb nail image.

When the group frame images to be used for analysis has been selected out of the groups consisting of a series of frame images, the thin-out data of the selected frame images is associated with the radiographing order information, and is sent to the WS 8 for analysis through the network communication section 56 (Step S18). For example, each of the pieces of thin-out data of a series of selected frame images is assigned such information as the identification ID for identification of the dynamic image, patient information, radiographed region, irradiation conditions, image reading conditions (frame interval, etc.), radiographing sequencer number, the number of frames, and date of radiographing (for example, such information is written into the header area of the image data using the file format of the DICO M (Digital Imaging and Communications in Medicine) multi-format). This data is then sent to the WS 8 for analysis through the network communication section 56. Further, analysis items are also sent to the WS 8 for analysis.

In the WS 8 for analysis, analysis is conducted based on the group of frame images having been received (Step S19).

The details of analysis are different for each radiographed region. The following describes the case of analyzing the lung field.

Analysis of the lung field is conducted in two ways. One is the analysis of calculating the feature value showing the local movement of the lung field. The other is the analysis of calculating the feature value showing the overall movement of the lung field. Further, the ventilation function is the object of analysis in some cases, and the blood flow function is the object of analysis in other cases.

In the analysis of calculating the feature value showing the local movement of the ventilation function in the lung field, the items (1) through (6) below can be mentioned. The following briefly describes the calculation procedure for each feature value. To clarify the processing required for analysis, the procedure of calculating the feature value from the raw data of the radiographed frame image is described. In the present embodiment, for the purpose of reducing the amount of data when the frame image is sent to the WS 8 for analysis and minimizing the processing time, each frame image is already subjected to binning processing as one type of thinning processing (i.e., images are already divided into the small areas of a prescribed size and signal values are averaged for each small area).

In the conventional method, warping is provided and pixels of different frame images are associated to calculate the feature value. In the analysis of the WS 8 for analysis, however, the process of warping is not provided. Instead, pixels showing the outputs of the detecting elements at the same position of the FPD 9a are associated with each other, and the feature value is calculated. A substantial reduction in processing time is achieved with the precision of feature value kept unchanged.

(1) Ventilation—Inter-Frame Differential Image

The inter-frame differential image can be calculated by applying the following processing to a series of frame images:

Binning processing→low-pass filtering in the direction of time axis→inter-frame difference processing→noise elimination As described above, binning processing refers to the process wherein, in each frame image, the image area is divided into the small areas in units of pixel blocks having a prescribed size to calculate the representative value of the signal value of the pixel within the area for each small area (for example, to work out an average). Without being restricted to the average value, the representative value can be a median, average value or mode. For the purpose of improving analysis precision, the size of the pixel block preferably conforms to the region to be analyzed and/or the feature value calculated from the analysis.

The low-pass filtering process in the direction of time axis is intended to extract the chronological fluctuation of the signal value caused by ventilation. For example, a cut-off frequency of 0.5 Hz is used for filtering.

In the inter-frame difference processing, the small areas at the same pixel positions of a series of frame images (the areas outputted from the detecting element at the same position of the FPD) are associated with one another, thereby calculating the differential value of the signal value between adjacent frame images for each small area, so that an inter-frame differential image is created.

When the still image of the inter-frame differential image is to be created, inhalation and expiration periods in a series of frame images are calculated by analyzing the density fluctuation of the entire lung field or changes in the diaphragm position. For each small area, an image is created by integrating the absolute value of the positive inter-frame differential value for the inhalation period, and by integrating the absolute value of the negative inter-frame differential value for the expiration period.

(2) Ventilation—Waveform Drawing

The ventilation—waveform drawing is calculated by applying the following processing to a series of frame images:

Binning processing→low-pass filtering in the direction of chronological axis→waveform drawing The binning processing and low-pass filtering in the direction of chronological axis are as described above (the same hereafter).

In the wave drawing, the small areas at the same pixel positions of a series of frame images (the pixel block areas outputted from the detecting element at the same position of the FPD) are associated with one another, and a coordinate plane is created for each small area wherein the time elapsed from the start of radiographing is plotted on the horizontal axis, and the average signal value of the pixels is plotted on the vertical axis. The waveform denoting the chronological fluctuation of the signal value showing the amount of ventilation is drawn by plotting the points of intersection between the time elapsed from the start of radiographing for each frame image and the average signal value calculated for that small area.

(3) Ventilation—Air Flow Velocity

The air flow velocity is a feature value representing the softness of the lung (lung compliance) in each the small area. The air flow velocity is calculated by applying the following processing to a series of frame images:

Binning processing→low-pass filtering in the direction of chronological axis→inter-frame difference processing→calculation of a representative value for inter-frame differential value (the maximum value or average value)

When the maximum value is used as a representative value, each of the maximum values for changes in signals (inter-frame differential values) in each of the expiration and inhalation periods is calculated for each small area as an indicator showing the maximum value of the air flow velocity in each of the expiration period and inhalation period, and a histogram representing the distribution of the ratio thereof (the maximum flow velocity ratio) is created. This is followed by the step of creating an image wherein each of the small areas in any one of the frame images is expressed in terms of the brightness or color in conformity to the maximum flow velocity ratio. These two images are compared and can be submitted as a result of analysis. This analysis is referred to as histogram analysis of the maximum flow velocity ratio.

Figure 11A:
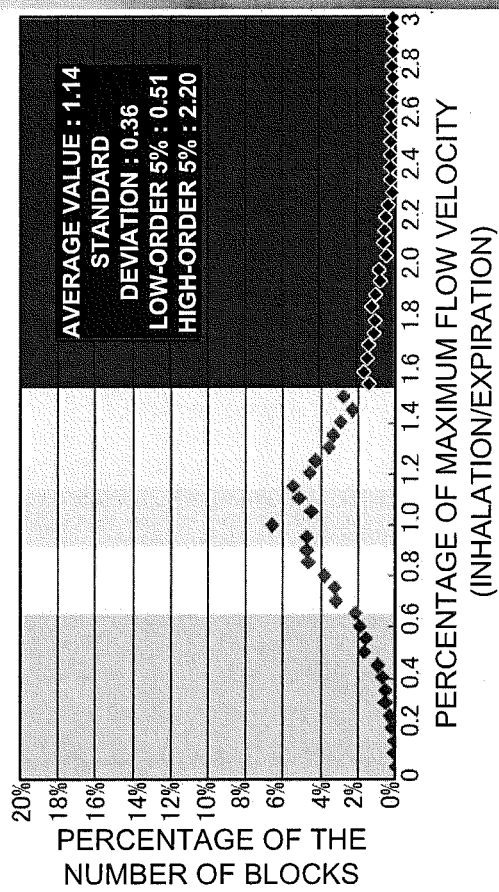
FIG. 11A is a diagram showing the result of analyzing the maximum flow velocity ratio when the block size is 2 mm×2 mm.

In the histogram analysis of the maximum flow velocity ratio, as shown in FIG. 11A through FIG. 11C, the ratio between the maximum value (absolute value) of the inhalation air flow velocity in each of the small areas and the maximum value (absolute value) of the expiration air flow velocity is displayed as a histogram. At the same time, an image is generated wherein the average value in the entire lung field as an indicator of determining the COPD, and the standard deviation are displayed. Further, each of the small areas on the still image is displayed in terms of brightness or color in conformity to the ratio, thereby providing the diagnostic information capable of easy identification of the distribution of lesions by a doctor.

(4) Amplitude in the Amount of Ventilation

Amplitude in the amount of ventilation can be calculated by applying the following processing to a series of frame images:

Binning processing→low-pass filtering in the direction of chronological axis→associating the small areas at the same pixel positions of a series of frame images (the pixel block areas outputted from the detecting element at the same position of the FPD) with one another, and calculating the maximum signal value (maximum value) minus the minimum signal value (minimum value) in one cycle of respiration for each small area.

(5) Inhalation Delay Time

Inhalation delay time can be calculated by applying the following processing to a series of frame images:

Binning processing→low-pass filtering in the direction of chronological axis→associating the small areas at the same pixel positions of a series of frame images (the pixel block areas outputted from the detecting element at the same position of the FPD) with one another, and analyzing the density fluctuation of the entire lung field and or changes in diaphragm position, thereby extracting the frame image at the resting expiration position, and calculating, from the frame image at the resting expiration position, the time until the difference from the signal value at the resting expiration position in inhalation exceeds a prescribed threshold value for each small area (6) Inhalation Time and Expiration Time Inhalation time and expiration time can be calculated by applying the following processing to a series of frame images:

Binning processing→low-pass filtering in the direction of chronological axis→associating the small areas at the same pixel positions of a series of frame images (the pixel block areas outputted from the detecting element at the same position of the FPD) with one another, and calculating the maximum signal value (maximum value) and the minimum signal value (minimum value) in one cycle of respiration for each small area→calculation on the assumption that the time from the maximum signal value to the minimum signal value is the expiration time, and the time from the minimum signal value to the maximum signal value is the expiration time In the analysis of calculating the feature value showing the local change of the signal caused by the blood flow in the lung field, the following items (7) through (10) can be mentioned. The following briefly describes the calculation procedure for each feature value. The procedure of calculating the feature value from the raw data of the radiographed frame image will be described. In the present embodiment, for the purpose of reducing the amount of data when the frame image is sent to the WS 8 for analysis and minimizing the processing time, each image is already subjected to binning processing (i.e., images are already divided into the small areas of a prescribed size and signal values have been averaged for each small area).

(7) Blood Flow—Inter-Frame Differential Image

The inter-frame differential image can be calculated by applying the following processing to a series of frame images:

Binning processing→high-pass filtering in the direction of time axis→inter-frame difference processing→noise elimination The high-pass filtering in the direction of time axis is intended to extract the chronological fluctuation of the signal value caused by blood flow. For example, a cut-off frequency of 0.7 Hz is used for filtering. Otherwise, processing is the same as described with reference to the aforementioned (1) "Ventilation—inter-frame differential image".

(8) Blood Flow—Waveform Drawing

The blood flow—waveform drawing can be calculated by applying the following processing to a series of frame images:

Binning processing→high-pass filtering in the direction of time axis→waveform drawing for each of the small areas The binning processing and high-pass filtering in the direction of time axis are the same as described above (the same hereafter).

The processing of waveform drawing is the same as that described with reference to the aforementioned (2) "Ventilation—waveform drawing".

(9) Amplitude in the Amount of Blood Flow

The amplitude in the amount of blood flow can be calculated by applying the following processing to a series of frame images:

Binning processing→high-pass filtering in the direction of time axis→associating the small areas at the same pixel positions of a series of frame images (the pixel block areas outputted from the detecting element at the same position of the FPD) with one another, and calculating the maximum signal value (maximum value) minus the minimum signal value (minimum value) in one cycle of heart beating for each small area

(10) Ventricle Contraction Delay Time

The inhalation delay time can be calculated by applying the following processing to a series of frame images:

Binning processing→high-pass filtering in the direction of time axis→associating the small areas at the same pixel positions of a series of frame images (the pixel block areas outputted from the detecting element at the same position of the FPD) with one another, and analyzing the density fluctuation of the ventricle area or changes in the cardiac wall position, thereby extracting the frame image corresponding to the termination of the ventricle expansion phase, and calculating, from the frame image corresponding to the termination of the ventricle expansion phase, the time until the difference from the signal value in the termination of the ventricle expansion phase exceeds a prescribed threshold value in the phase of ventricle contraction for each small area In the analysis of calculating the feature value showing the movement of the entire lung field, the following items (11) through (15) can be mentioned. The following briefly describes the calculation procedure for each feature value. The procedure of calculating the feature value from the raw data of the radiographed frame image will be described. In the present embodiment, for the purpose of reducing the amount of data when the frame image is sent to the WS 8 for analysis and minimizing the processing time, each image is subjected to binning processing. However, the following feature values can be calculated independently of whether binning processing is applied or not.

(11) Diaphragm Movement Analysis

The diaphragm movement can be calculated by applying the following processing to radiographed frame images:

Extraction of diaphragm position from each of frame images by image analysis→calculation of the movement by tracing the diaphragm position of each frame image

(12) Thorax Movement Analysis

The thorax movement can be calculated by applying the following processing to radiographed frame images:

Extraction of the position of the upper thorax (upper ribs (the 2nd through 6th ribs)) and lower thorax (lower ribs (the 7th through 10th ribs)) from the frame image by image analysis→calculation of the movement by tracing the upper thorax and lower thorax of each frame image

(13) Respiration Rate and Breathing Cycle

The respiration rate and breathing cycle can be calculated by applying the following processing to radiographed frame images:

Calculate the breathing cycle from the change in the diaphragm position (distance from the lung apex to the diaphragm) obtained from each image by image analysis or from the change of the signal in the overall lung field subsequent to low-pass filtering (time interval from the maximum value of the signal value (average signal value) to the next minimum value). Then calculate the respiration rate per unit time from the reciprocal of the breathing cycle.

(14) Heart Rate and Cardiac Cycle

The heart rate and cardiac cycle can be calculated by applying the following processing to radiographed frame images:

Calculate the cardiac cycle from the change in the cardiac wall position obtained from each image by image analysis, or from the change of the signal in the overall lung field subsequent to low-pass filtering (time interval from the maximum value of the signal value (average signal value) to the next minimum value). Then calculate the respiration rate per unit time from the reciprocal of the cardiac cycle.

(15) Calculation of Spirometric Equivalent Value

Calculate the chronological fluctuation waveform of the diaphragm position and obtain the equivalent of FEV 1.0% (forced expiratory volume in one second percent). Get the change in the area of the lung field from the fluctuation in the thorax and diaphragm positions, and multiply the result by the change in the separately measured thickness of the chest, thereby calculating the value equivalent to VC (vital capacity).

Upon completion of analysis, analysis result data is sent to the console 5 through the communication network N in the WS 8 for analysis (Step S20). In the console 5, when the analysis result data has been received by the network communication section 56, the received analysis result data is sent to the PACS10 in the form associated with the radiographing order information (Step S21). This terminates the radiographing and analysis processing. It should be noted that the frame image data used for the analysis of feature values cannot be used for radiographic interpretation of the lesion based on the density gradation such as in the still image. Therefore, for the purpose of reducing the amount of stored data, only the calculated feature value data is preferably saved, without saving the frame image data used for the analysis of feature values. It is also possible to make such arrangements that, in the WS 8 for analysis, the analysis result data is associated with the radiographing order information received from the console 5, and these pieces of data are sent to the PACS10 from the WS 8 for analysis.

In the PACS10, the analysis result data having been received is associated with the radiographing order information and is stored in the HDD of the server device. In response to the request from the radiographic interpretation terminal, the result of analysis is displayed on the display section of the radiographic interpretation terminal.

In a conventional system wherein the feature values related to the relevant dynamic items are calculated based on a series of frame images captured by radiographing dynamic image, and the result thereof is submitted as diagnosis support information, it has been considered essential to provide processing of so-called warping for mutual associations among the areas wherein the same portion of a subject is drawn, in a plurality of frame images for the purpose of enhancing diagnosis precision (e.g., Japanese Unexamined Patent Application Publication No. 2003-298939 and Japanese Unexamined Patent Application Publication No. 2009-153678). To perform the process of warping, it is necessary to divide one frame image into a plurality of small areas and then extract, for each frame image, the small area containing the same drawn portion as that of the structure drawn in each of the small areas in the relevant frame image. In the process of warping, faithful (uniform) reproduction of the density of the relevant structure for each of the frame images is generally essential for the sake of positioning based on the spatial density fluctuation due to the structure inside the lung field. This requires the output fluctuation of pixels of the detector to be minimized wherever possible (hence, various corrections including offset correction, gain correction, correction of defective pixel and lag correction must be made to correct the fluctuation). Such corrections require much time. Further, high-precision warping requires images of higher resolution, hence a detector of smaller pixel size. This results in an increased data capacity for each frame image and a substantial reduction in the overall data capacity of the subject to be observed. This makes it necessary to prepare hardware such as a high-capacity memory or high-speed CPU. The processing time will also be increased.

The present inventors have made concentrated study efforts to find out that the analysis result of the equivalent level can be obtained, without warping, by comparing the differences among a series of frame images in the radiographing dynamic image, in units of individual detecting elements of the FPD or in units of the pixel blocks wherein a plurality of pixels are put together.

Taking an example from the lung field, the following describes why the analysis result of the equivalent level can be obtained without warping.

The fluctuations of the signal value in the direction of body thickness (z-axis direction: lateral side) will be described first.

Figure 8:
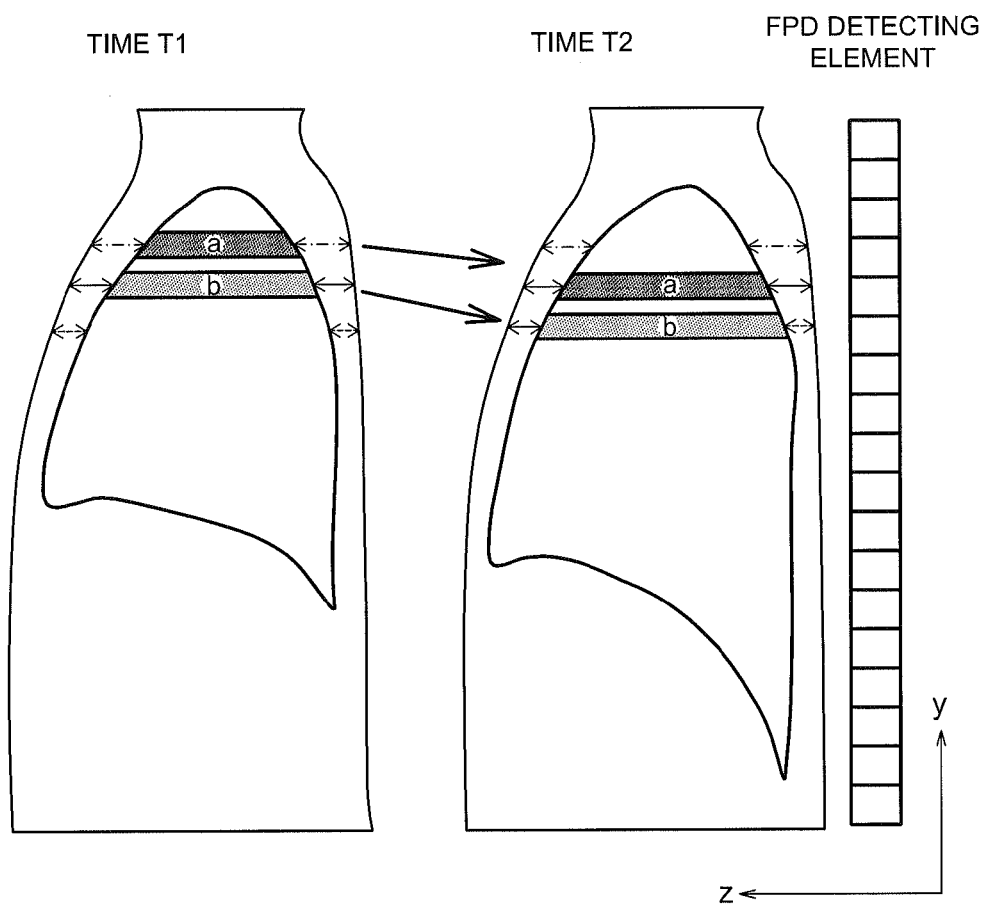
FIG. 8 is a diagram showing the chronological change on the side of the chest.

FIG. 8 schematically shows the lung field in the direction of body thickness (z-axis direction) at time T1 representing the resting expiration position, the lung field in the direction of body thickness at time T2 representing the position of inhalation at rest after the process of inhalation from time T1, and the FPD at the detecting element position (in the direction of body axis (y-axis direction)). In FIG. 8, alveolus "a" and alveolus "b" in the y-axis direction are moved down by inhalation. This is an example of agreement in the positions between the alveolus b in the y-axis direction at time T1 and the alveolus a in the y-axis direction at time T2.

The alveolus in the lung field is moved by inhalation. The same alveoluses are positioned among the frame images and the difference of signal values is taken after warping. The amount of attenuation of the X-ray in the z-axis direction outside the lung field varies according to the position of the lung field in the y-axis direction. Accordingly, if the alveolus is positioned, the difference in the amount of attenuation of the X-ray outside the lung field will be added as an error factor to the increment of the signal due to the fluctuation in the density of the alveolus caused by respiration.

For example, in FIG. 8, alveoluses b are positioned between the frame image at time T1 and the frame image at time T2, and difference in the signal values is taken subsequent to warping. This differential value includes the difference between the amount of attenuation of the X-ray outside the lung field indicated by the solid arrow of time T1 and that of the X-ray outside the lung field indicated by the dotted-line arrow of time T2. The difference in the amount of attenuation of the X-ray outside the lung field will be added as an error to the fluctuation of in the density caused by respiration between the same alveoluses. This results in deterioration of the precision in calculating the amount of fluctuation in the signal caused by changes in the alveolus density.

The following calculates the pixel (pixel block) wherein the alveolus b of the frame image at time T1 and alveolus a of the frame image at time T2 are drawn without alveolus positioning or warping, i.e., the difference of the signal value outputted from the detecting element (detecting element group) of the FPD at the same position. In this case, the differential value is calculated for the same position in the y-axis direction of the lung field, although alveoluses drawn on this pixel (pixel block) are different. Accordingly, there is no change in the amount of attenuation of the X-ray outside the lung field, as shown in FIG. 8. Thus, when the differential value of the signal value has been calculated among different alveoluses, the change of the signal due to the fluctuation in density among different alveoluses (difference in density between "a" and "b" at the same timing in FIG. 8) will be added as an error to the change of the signal due to the difference in the fluctuation of density caused by respiration among the same alveoluses.

"The change of signal due to the fluctuation of density among the alveoluses whose positions in the y-axis direction position inside the lung field are different" is equal to or below "the change of the signal due to the fluctuation in the amount of attenuation of the X-rays outside the lung field whose position in the y-axis directions are different". Accordingly, if the difference is taken directly in units of the pixels of the FPD without positioning or warping among frame images, the time and effort of processing will be saved and the change of the signal due to the fluctuation of density of the alveolus can be calculated on the same level of errors.

Especially error components present for each of the pixels or small areas are added and offset when calculating the information on the amount of ventilation in the entire lung field. If the process of warping is applied in calculating the feature value for the ventilation and blood flow on the entire lung field, this will bring about only the negative effect of the processing time being prolonged by warping.

Figures 9, 10:
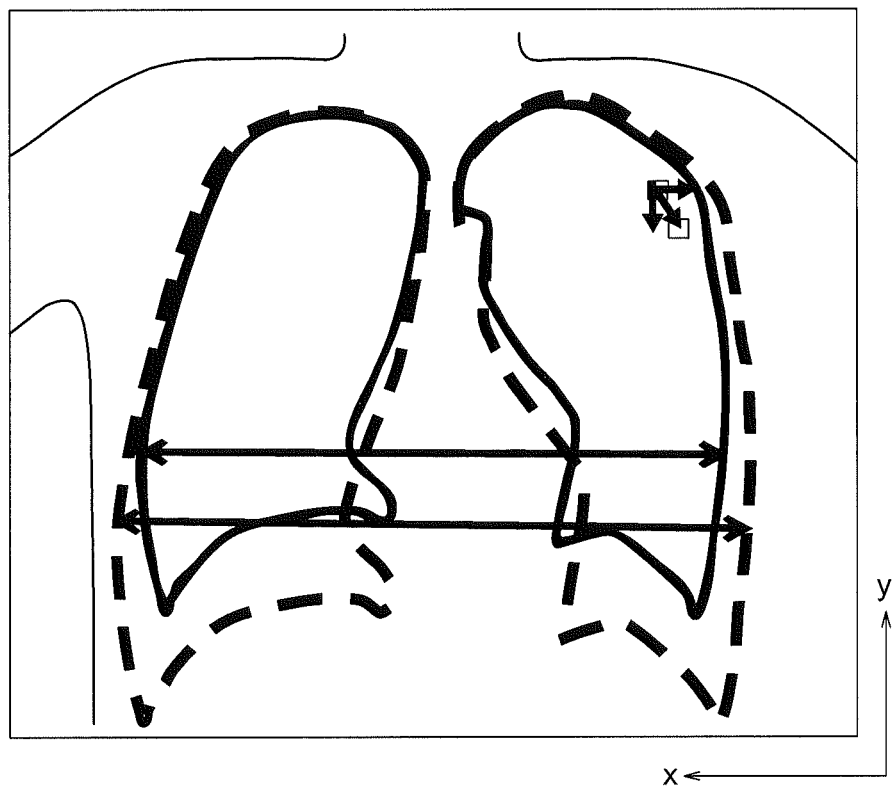
FIG. 9 is a diagram showing the chronological change on the front of the chest.
FIG. 10 is a diagram showing the result of analyzing the representative items in the process of analysis when the block size of a small area is changed, and the result of evaluating the processing time.

The following examines the x-y axis direction. FIG. 9 shows the lung field as viewed from the front (x-y axis direction). The solid line of FIG. 9 indicates the frame image at time T1 of FIG. 8 as viewed in the x-y axis direction (front). The dotted line of FIG. 9 indicates the frame image at time T2 of FIG. 8 as viewed in the x-y axis direction (front).

As shown in FIG. 9, normally at the time of inhalation, the alveolus moves toward the lower left in the case of the left lung field and toward the lower right in the case of the right lung field. This movement is divided into the movement in the vertical direction (y-axis direction) and that in the horizontal direction (x-axis direction). Warping of the movement of the alveolus in the y-axis direction is as described above.

The following describes the movement of the alveolus in the x-axis direction at the time of ventilation at rest.

In ventilation at rest, the change of the thorax is on the order of 10 mm at most. In this case, when changes from the resting expiration position to the resting inhalation position are taken into account, the movement in the x-axis direction is the greatest in the alveolus located immediately inside the thorax, and is on the order of 5 mm. When dynamic images are captured at a frame rate of 3.75 frames per second to calculate the inter-frame differential value, the movement of the alveolus between adjacent frame images is further reduced, and is negligible. At the time of ventilation at rest, the movement in the x-axis direction is small. Changes in signal values are the same independently of whether warping is provided or not. Thus, warping is not necessary in the x-y direction.

In conformity to the aforementioned findings, it is sufficient to perform calculation in units of pixels denoting the output of each detecting element of the FPD or in units of small areas without warping. Therefore, without restricting the format of the output signal from the FPD, the WS 8 for analysis is capable of handling frame images generated by the FPD 9a compatible with the radiographing dynamic image method used by each company, e.g., frame images that have underwent binning processing. To put it another way, the WS 8 enables an open system.

Incidentally, radiographing dynamic image has a problem in that the number of frame images used for analysis shows a drastic increase over than of the still image, and the processing time also undergoes a drastic increase. The present inventors have made concentrated study efforts to solve this problem.

In the conventional system (CAD) wherein the candidates for the abnormal shadows of the chest and udder are detected and are supplied to a doctor as diagnosis support information, the detection algorithm is supplied to the original image data. Thus, importance has been attached to the efforts for ensuring that the density resolution and the pixel size of the image per se to which the algorithm is applied will match the detection algorithm (pixel size and density resolution being high-definition and high-resolution).

Further, in the conventional system, a thin-out image has been created from the original image. Such a thin-out image has been used only in the preliminary phase of the detection process such as the phase of checking if the area of interest of the subject lies within the range of analysis or not, or the phase of calculating the gradation processing conditions for ensuring that the density range of the image to be detected lies within the range of density conforming to the detection algorithm. In the detection by a CAD, such a thin-out image has been discarded, without being utilized.

In the meantime, as described above, the feature value analysis of the dynamic image mainly based on processing of the differential value among adjacent frames. Thus, the feature value analysis of the dynamic image does not require the strict output value of each pixel as in the analysis by the conventional CAD, wherein the absolute output value of each pixel is compared with the threshold value or fine structures are extracted, for example. Further, the present inventors have found out that there is no adverse effect of the pixel size of the individual image.

The present inventors have made concentrated study efforts to find out that the same result can be obtained by changing the computation (analysis) in unit of pixel into the computation in units of small areas of a specific pixel block size (block size) (computation using one pixel value in each of the small areas, and computation using the representative value (average value, etc.) of the pixel values in the small area). The present inventors have also found out that a substantial reduction in the amount of data required for the computation of the analysis and a drastic cutdown of the processing time can be achieved by this procedure.

FIG. 10 shows the result of analyzing the representing items in the aforementioned process of analysis and the result of evaluating the processing time, when the pixel block size of the small area is changed in the range from 0.5 millimeter square through 10 millimeter square.

In this case, the object items include the inter-frame differential image of the amount of ventilation, histogram analysis of the maximum flow velocity ratio and inter-frame differential image of the amount of blood flow. The image radiographed under the identical irradiation conditions and image reading conditions such as an exposure dose and frame rate are used as frame images. In FIG. 10, the frame rate is 7.5 frames per second, a dosage on the input surface in ten seconds is 0.2 mGy, and the pixel size of the FPD $9a$ is 200 µm. In FIG. 10 (and FIG. 11A and FIG. 11B to be described later), the evaluation results of A or higher indicate the precision that can be used for diagnosis, showing that the feature value can be calculated. The degree of analysis precision is shown in its ascending order (low to high): A→B→C. Further, the processing time "x" indicates that the processing time is too long to be of practical use. The symbols A and higher indicate that the processing time is within the range tolerable for practical use. When the processing time lies within this range, a considerable reduction in processing time can be achieved, as compared to the case of using the entire pixel data, even if the level is "x". Accordingly, its use is not entirely rejected.

As shown in FIG. 10, when the block size was 0.5 through 1 square millimeter, a high precision was obtained in the results of all analyses including calculation of the inter-frame differential value of the amount of ventilation, histogram analysis of the maximum flow velocity ratio and inter-frame differential value of the amount of blood flow. When the block size was 2 millimeter square, satisfactory results were obtained in diagnosis although the analysis precision was slightly inferior to that when the block size is 0.5 through 1 millimeter square. When the block size was 5 millimeter square, poorer analysis precision was recorded for all items. However, analysis precision required for diagnosis was ensured. When the block size was 10 mm×10 mm, analysis precision required for diagnosis could not be obtained. In the meantime, the processing time was increased as the block size was decreased, as shown in FIG. 10.

The following describes the evaluation of the analysis result by giving an example.

FIG. 11A through FIG. 11C show an example of the result of histogram analysis of the maximum flow velocity ratio when the block size was 2 mm×2 mm, 5 mm×5 mm and 10 mm×10

When the block size was 0.5 mm×0.5 mm and 1 mm×1 mm, there was almost no change from the histogram of FIG. 11A.

The analysis result when the block size was 2 mm×2 mm in FIG. 11A is compared with that when the block size was 5 mm×5 mm in FIG. 11B. A slight change is observed in the configuration of the histogram. The analysis result when the block size was 2 mm×2 mm in FIG. 11A is compared with that when the block size was 10 mm×10 mm in FIG. 11C. A drastic change is observed in the configuration of the histogram. This denotes a substantial reduction of analysis precision. Thus, from the viewpoint of analysis precision, the block size is required to be 5 mm×5 mm or less, in particular 2 mm×2 min or less. In the meantime, from the viewpoint of processing time the processing time is increased as the block size is decreased, as shown in FIG. 10. Thus, from the viewpoint of maintaining analysis precision and reducing the processing time, the block size preferably lies in the range of approximately 2 mm×2 mm through 5 mm×5 mm in the ventilation analysis for the lung field.

Further, from the viewpoint of removing a change of the signal caused by rib movement, it is preferable that the block size is about 2 millimeter. For example, if the block size is increased to include a plurality of the ribs for the purpose of removing impact of a change of the signal caused by rib movement, the block size wherein a plurality of the ribs are included is 50 through 100 millimeters since the rib size is in the range of 10 mm through 20 mm. This denotes an excessively low resolution and is not suited for local analysis. If the block size is increased so as to include the movement of one rib plus rib movement during respiration at rest, the block size will be 15 through 20 millimeters since the rib size is from 10 mm through 20 mm, and the rib movement during respiration at rest is several millimeters. This also means an excessively low resolution and is not suited for local analysis. Further, it is difficult to separate the small area so that other ribs are not included. To solve this problem, the block size is reduced to some extent to detect the area wherein the change of the signal due to the rib is greater than that in the surrounding. This area is excluded from the analysis or is replaced by the cyclic signal value, thereby removing the impact of ribs. The block size in this case is preferably on the order of 2 mm×2 mm through 5 mm×5 mm.

From the aforementioned viewpoint, the block size is frequency on the order of 2 2 mm×2 min through 5 mm×5 mm for analysis of ventilation in the lung field.

Further, the present inventors have studied the impact of the frame rate of FPD $9a$ upon analysis.

FIG. 12A through FIG. 12B show the analysis results of analyzing the representative items in the aforementioned analysis, processing time, impact of thin-out procedure, and the result of evaluating the degree of radiation exposure of a patient when the frame rate of FPD $9a$ is changed in the range from two frames per second through 20 frames per second. FIG. 12A shows the evaluation result when the exposure dose is kept constant in each frame image. FIG. 12B shows the evaluation result when the overall exposure dose in one radiographing dynamic image operation is kept constant (equivalent to an incoming exposure dose of 0.2 mGy for ten seconds of radiographing). In both FIG. 12A and FIG. 12B, the pixel size is 200 μm, and the block size is a square of 2 mm×2 mm.

When the exposure dose of each frame image is kept constant, the feature value of the precision capable for use in diagnosis can be obtained for the amount of ventilation and histogram analysis of the maximum flow velocity ratio if the frame rate is 3.75 frames per second or more, as shown in FIG. 12A. To get the feature value of the precision capable for use in diagnosis, 10 frames per second or more were needed for the ventilation delay time, and 30 frames or more were necessary for blood flow delay time. In the meantime, for the processing time, the length of time was increased as the frame rate was increased, and the practical requirements could not be met by 15 frames per second or more. It should be noted that, when the pixel interval is thinned out to ⅛, the processing time was satisfactory at all the frame rates. For the radiation exposure dosage of the patient, the length was increased as the frame rate was increased. The dosage exceeded twice the normal incoming surface dosage during the radiographing of still X-ray images of the chest at a frame rate of 30 frames per second or more, with the result that the permissible range was exceeded.

In radiographing dynamic image, when the overall exposure dose is kept constant and the exposure dose per frame image is made to reduce with the increase in the frame rate, the evaluation result in each analysis item is lower than that of FIG. 12A at 15 frames per second or more, as shown in FIG. 12B. This is because the S/N ratio of each frame image is worsened and the image quality is deteriorated with the increase in the frame rate.

The following describes the evaluation of the analysis result of FIG. 12 by giving an example.

FIG. 13A through FIG. 13E show an example of the analysis result in the histogram analysis of the maximum flow velocity ratio in radiographing dynamic image when the overall exposure dose is kept constant and the frame rate is changed in the range from 2 through 30 frames per second.

As shown in FIG. 13A, when the frame rate is 2 frames per second, differences occur to the analysis result as compared to the case wherein the frame rate is 3.75 frames per second. These differences are found in the average value which has changed from 1.15 to 1.32 (an increase of 15%), and the distribution value which has changed from 0.38 to 0.52 (an increase of 37%). There is an increase in the small area exhibiting an abnormal value (the area wherein the brightness conforming to the maximum flow velocity ratio is not superimposed on the still image in the lung field area of the FIG. 13A through FIG. 13E). The level of analysis precision is reduced. When the maximum value for inter-frame differential value is to be calculated in each of the inhalation and expiration and the maximum value of the inter-frame differential value is lower that a prescribed threshold value, the relevant small area as an abnormal value is excluded from the object of analysis for the purpose of minimizing the impact of noise. To put it more specifically, since there is an increase in the signal value at the time of inhalation, the value is assumed as normal if the maximum value of the inter-frame differential value is greater than a prescribed positive threshold value. Since there is a decrease in the signal value at the time of expiration, the value is assumed as normal if the maximum value of the inter-frame differential value is smaller than a prescribed negative threshold value. All values except for the aforementioned ones are evaluated as abnormal values.

When the frame rate is 3.75 frames per second or more, approximately the same analysis result can be obtained for an adult person at the average respiration rate (15 through 20 respirations at rest, wherein the breathing cycle is 3.33 sec. in the case of 18 respirations at rest), as shown in FIG. 13B through FIG. 13E. However, when consideration is given to a rare case of a patient suffering from tachypnea (a patient suffering from higher respiration rate per unit time; i.e., 24 through 40 respirations per minute, wherein the breathing cycle is 1.5 sec. when the respiration rate is assumed as 40 respirations per minute), the frame rate is preferably 7.5 frames per second or more. Even if there has been a decrease in dosage per frame image at a high frame rate, noise is reduced by increasing the number of taps (estimated number of times) used in the low-pass filter in the direction of chronological axis by the increased number of frame images, and deterioration of the analysis result can be suppressed.

However, implementation of a high frame rate requires an increase in the speed of reading the data of the FPD 9a, reduction of transfer time, and a complicated structure of the X-ray generator for outputting short pulses. This will result in an increased hardware cost. Thus, when the overall dosage is made constant, there is not much advantage in achieving a high frame rate in the analysis of ventilation function.

For example, a tube voltage of 100 kV, tube current of 50 mA, a pulse width of 2 ms, and an additional filter A of 10.5 mm+Cu0.1 mm provide an example of radiographing conditions in the chest radiographing dynamic image wherein SID=200 cm (subject thickness is assumed as 20 cm) and the frame rate is 7.5 frames per second. In this case, the exposure dose per frame image of the X-ray pulse is 0.1 mAs (=50 mA×0.002 s). If the exposure dose per frame image has been changed to conform to the frame rate for the purpose of ensuring a constant overall dosage, the exposure dose of the X-ray pulse per frame image at a frame rate 15 frames per second is 0.05 mAs, and the exposure dose of the X-ray pulse per frame image at a frame rate 30 frames per second is 0.025 mAs. However, it is difficult to control the X-ray pulse width at 1 ms. An attempt to reduce the tube current will increase the length of the time constant for discharging the electric charge stored in the capacitor located between the anode and cathode of the X-ray tube. Since this results in a gradual decrease of the tube voltage, it will become necessary to provide a circuit for causing an abrupt discharge of the aforementioned electric charge. This will increase the device production cost. Thus, from the viewpoint of X-ray pulse control, a low frame rate is more advantageous.

Generally, the residual image (lag) in the FPD is reduced exponentially with respect to time (radiographing interval). Even if the exposure dose per frame image has been changed to conform to the frame rate to ensure constant overall dosage, i.e., even if the dosage has been reduced in inverse proportion to the frame rate, a smaller frame rate is more advantageous from the viewpoint of visibility of the residual image. Accordingly, in ventilation analysis, the frame rate is preferably in the range of 3.75 through 7.5 frames per second.

FIG. 14A through FIG. 14D show an example of the result of analyzing the inter-frame differential image (blood cardiac output timing) in radiographing dynamic image when the overall exposure dose is kept constant and the frame rate is changed in the range of 3.75 through 30 frames per second.

Figure 14A:
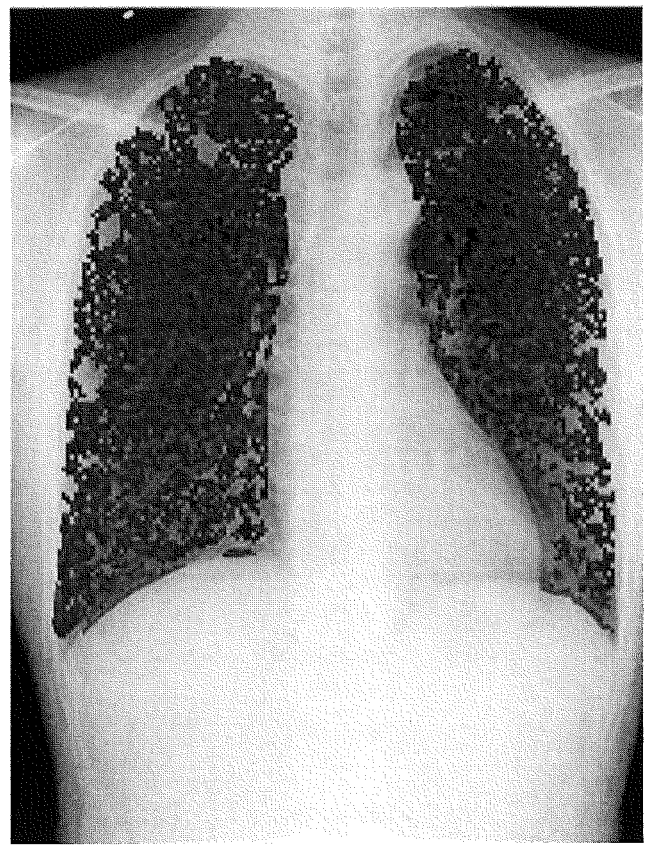
FIG. 14A is a diagram showing an example of an inter-frame differential image synchronized with blood flow beating when the block size is 2 mm×2 mm and the frame rate is 3.75 frames per second, with the overall exposure dose kept constant.
Figure 14B:
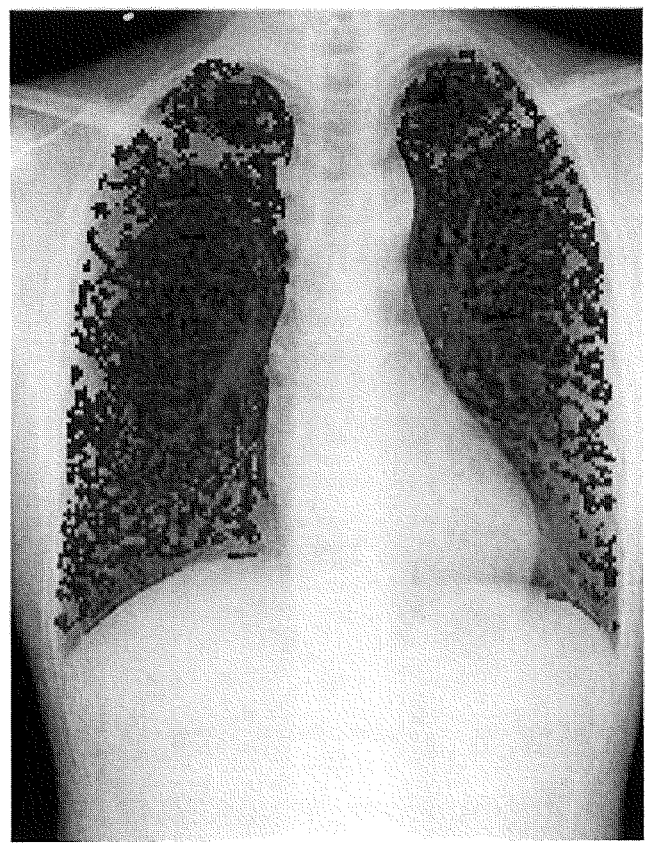
FIG. 14B is a diagram showing an example of an inter-frame differential image synchronized with blood flow beating when the block size is 2 mm×2 mm and the frame rate is 7.5 frames per second, with the overall exposure dose kept constant.
Figure 14C:
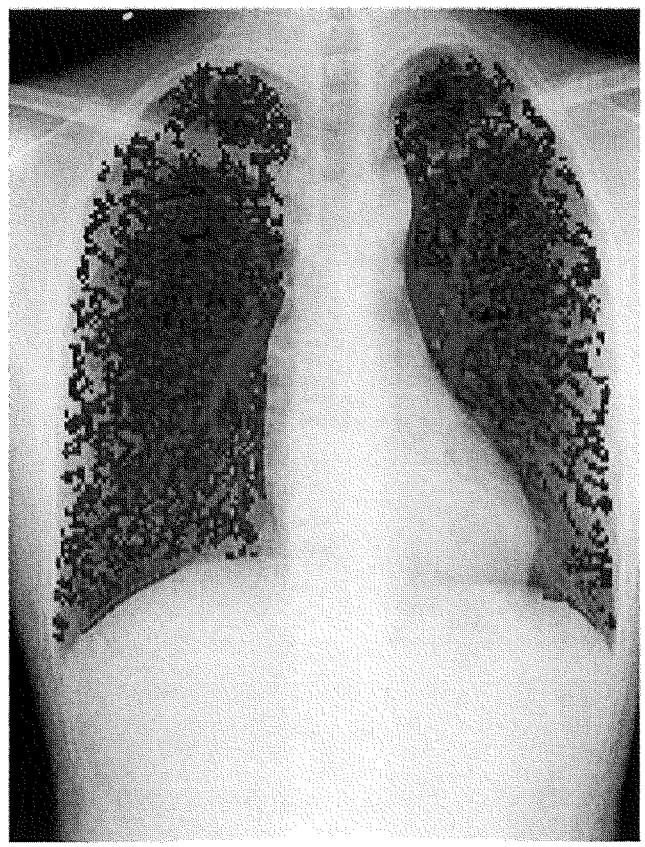
FIG. 14C is a diagram showing an example of an inter-frame differential image synchronized with blood flow beating when the block size is 2 mm×2 mm and the frame rate is 15 frames per second, with the overall exposure dose kept constant.
Figure 14D:
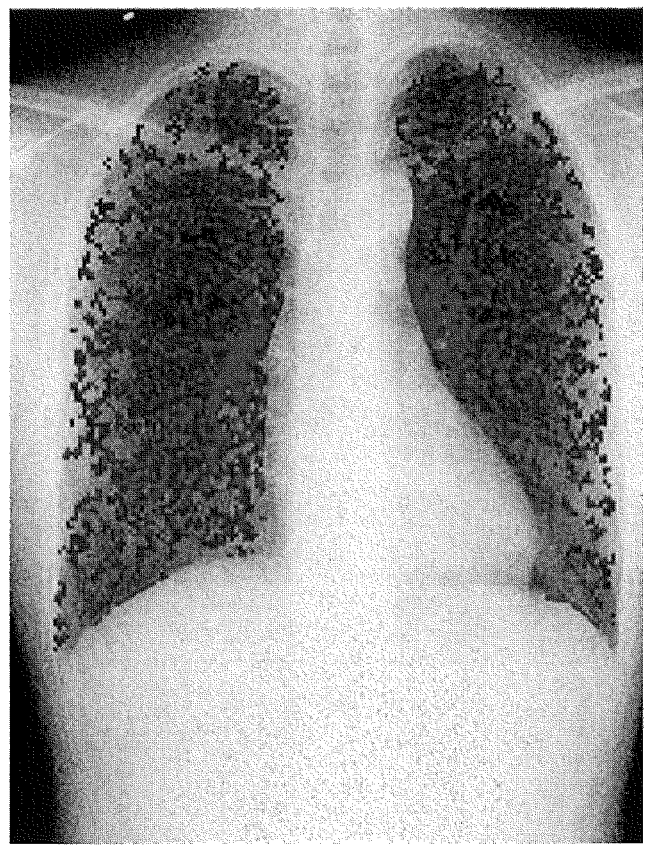
FIG. 14D is a diagram showing an example of an inter-frame differential image synchronized with blood flow beating when the block size is 2 mm×2 mm and the frame rate is 30 frames per second, with the overall exposure dose kept constant.

When the frame rate is 3.75 frames per second, frame image intervals are excessive and cardiac output timing may not be captured in some cases. When the frame rate is 7.5 frames per second or 15 frames per second, the cardiac output timing of the blood can be captured for the image of an adult person having an average pulse rate (50 through 100 times per minute at rest; cardiac cycle is 1.0 sec. for 60 times per minute), as shown in FIG. 14B and FIG. 14C. However, when consideration is given to a rare case of a patient suffering from tachycardia (a patient suffering from higher pulse rate per unit time; i.e., 100 through 120 pulses per minute, wherein the cardiac cycle is 0.5 sec. when the pulse rate is assumed as 120 pulses s per minute), the frame rate is preferably 15 frames per second or more. When the frame rate 30 is frames per second, noise is increased due to a smaller amount of dosage per frame image. This shows deterioration of the inter-frame differential image quality. Thus, in the blood flow analysis, the frame rate is preferably in the range of 7.5 through 15 frames per second.

The following studies the impact of the binning processing and simple thinning processing upon analysis. The histogram analysis of the maximum flow velocity ratio, inter-frame differential image of ventilation and blood flow inter-frame differential image when the binning processing and simple thinning processing have been applied will be compared, and impact of the two forms of processing will be studied.

FIG. 15A through FIG. 15C shows an example of the histogram analysis result of the maximum flow velocity ratio, ventilation inter-frame differential image and blood flow inter-frame differential image when binning processing and simple thinning processing have been applied. The analysis shown in FIG. 15A uses a dynamic image wherein the frame rate is 7.5 seconds per frame, and the overall dosage (incoming surface dosage in radiographing for 10 seconds) is equivalent to 0.2 mGy. The upper half of FIG. 15A shows the case wherein binning processing is applied to a square of 2 mm×2 mm, while the lower half of FIG. 15A shows the case wherein simple thinning processing has been applied at intervals of 2 mm. The upper half of FIG. 15B shows the case wherein binning processing is applied to a square of 2 mm×2 mm, while the lower half of FIG. 15B shows the case wherein simple thinning processing has been applied at intervals of 2 mm. The upper half of FIG. 15C shows the case wherein binning processing is applied to a square of 2 mm×2 mm, while the lower half of FIG. 15C shows the case wherein simple thinning processing has been applied at intervals of 2 mm.

As shown in FIG. 15A and FIG. 15B, in the histogram analysis of the maximum flow velocity ratio and ventilation inter-frame differential image, there is not much difference between binning processing and simple thinning processing for the analysis result. To be more specific, in ventilation analysis, there is not much difference of impact between binning processing and simple thinning processing. In the meantime, in the blood flow inter-frame differential image, noise on the image is greater in simple thinning processing than in binning processing, as shown in FIG. 15C. There is an increase in the small area (the area wherein the inter-frame differential value is not added in the still image of the lung field area of FIG. 15C) wherein blood flow information cannot be detected. Thus, in the analysis of ventilation function, any of the binning processing and simple thinning processing can be applied (any of the binning processing and simple thinning processing can be applied in the aforementioned analysis items). However, in the analysis of blood flow function, binning processing is preferably applied.

If binning processing is applied, the impact of the fluctuation of individual pixels will be mitigated by averaging of the signal values in the small area. This increases the possibility wherein the processing of corrections such as offset correction, gain correction, defective pixel correction can be omitted. A substantial reduction in the processing time can be achieved.

To check positioning, the image subjected to binning processing and simple thinning processing can be re-used for analysis. This ensures a substantial reduction in the processing time.

For example, in the fluoroscopic FPD compatible with radiographing of the existing moving image, the FPD itself ensures that the data subjected to binning processing of 2×2 pixels, for example, is outputted to the display device and is displayed on a real-time basis for use in checking the positioning of the surgical instrument and others. Thus, this type of output signal can be used directly for the analysis of the feature value. This indicates that feature values for a moving subject can be analyzed by using the output signal of the existing radiographing device.

In the above description of the first embodiment, a console 5 is arranged in each radiographing room and radiographic operations in the radiographing room are controlled by the console 5 of each radiographing room. As in the diagnosis support information generation system 200 of FIG. 16, it is also possible to make such arrangements that one or a plurality of consoles 5 are installed out of the radiographing room and the operation console 6 of each radiographing room can be connected with the access point AP so that each console 5 can control the radiographic operations in any of radiographing rooms R1 through R3.

In the diagnosis support information generation system 200 of FIG. 16, for example, the radiographing management table 521 of each console 5 has such items as "radiographing room NO.", "tube type", "Bucky's ID", "FPD ID" and "image reception time", and this system is capable of storing the tube type of the radiation source installed in the radiographing room of the radiographing room number associated with each radiographing mom number, the Bucky's ID of the Bucky's radiographic device, FPD ID of the FPD currently mounted on the Bucky's radiographic device, FPD ID of the FPD currently present in the radiographing room, and image reception time. In the Bucky's radiographic device of each radiographing room, when the FPD has been mounted in position, an FPD ID is acquired from the mounted FPD, and the radiographing room number, FPD ID and Bucky's ID are sent to each console 5. Similarly, in the cradle 4 of each radiographing room, when the FPD has been mounted in position, an FPD ID is acquired from the mounted FPD, and the radiographing room number and FPD ID are sent to each console 5. This configuration allows each console 5 to capture the situations in each of the radiographing rooms R1 through R3, and to determine the radiographing room wherein radiographing operations can be performed in conformity to the specified radiographing order information.

For example, in each console 5, when radiographing order information for specifying the radiographing dynamic image operation has been specified, the control section 51 can be used to determine in advance whether or not the radiographing dynamic image operation can be performed in each radiographing room based on the information stored in the radiographing management table 521, for example, the information on the types of the X-ray tube and FPD present in the radiographing room. Then the display section 54 indicates the selection screen showing the radiographing room wherein the radiographing operation is possible. It is also possible to make such arrangements that the selection screen indicates the tube type of the radiation source in each radiographing room and the types of the Bucky's radiographic device and FPD so that the operator can easily select the radiographing room wherein radiographing operation can be performed in conformity to the radiographing order information. It is also possible to make such arrangements that the display section 54 indicates the selection screen to enable the operator to select a radiographing room. Decision is made to determine whether or not radiographing operation can be performed in the selected radiographing room. If the radiographing operation cannot be performed, an alarm message is displayed. Such control enables the operator to perform radiographic operation in conformity to the radiographing order information without fail, even if the console 5 and radiographing room exhibit an m-to-n correspondence, not a one-to-one correspondence. This also prevents the operator from using a radiation source incapable of radiographing dynamic image, or from using a wrong FPD to start radiographic operations. If a radiographing room has been selected, the control section 51 causes the radiation source and FPD of the selected radiographing room to be started.

It should be noted that other operations in the diagnosis support information generation system 200 are the same as those described with reference to the diagnosis support information generation system 100.

Embodiment 2

The following describes the second embodiment of the present invention.

The structure will be described first.

Figure 17:
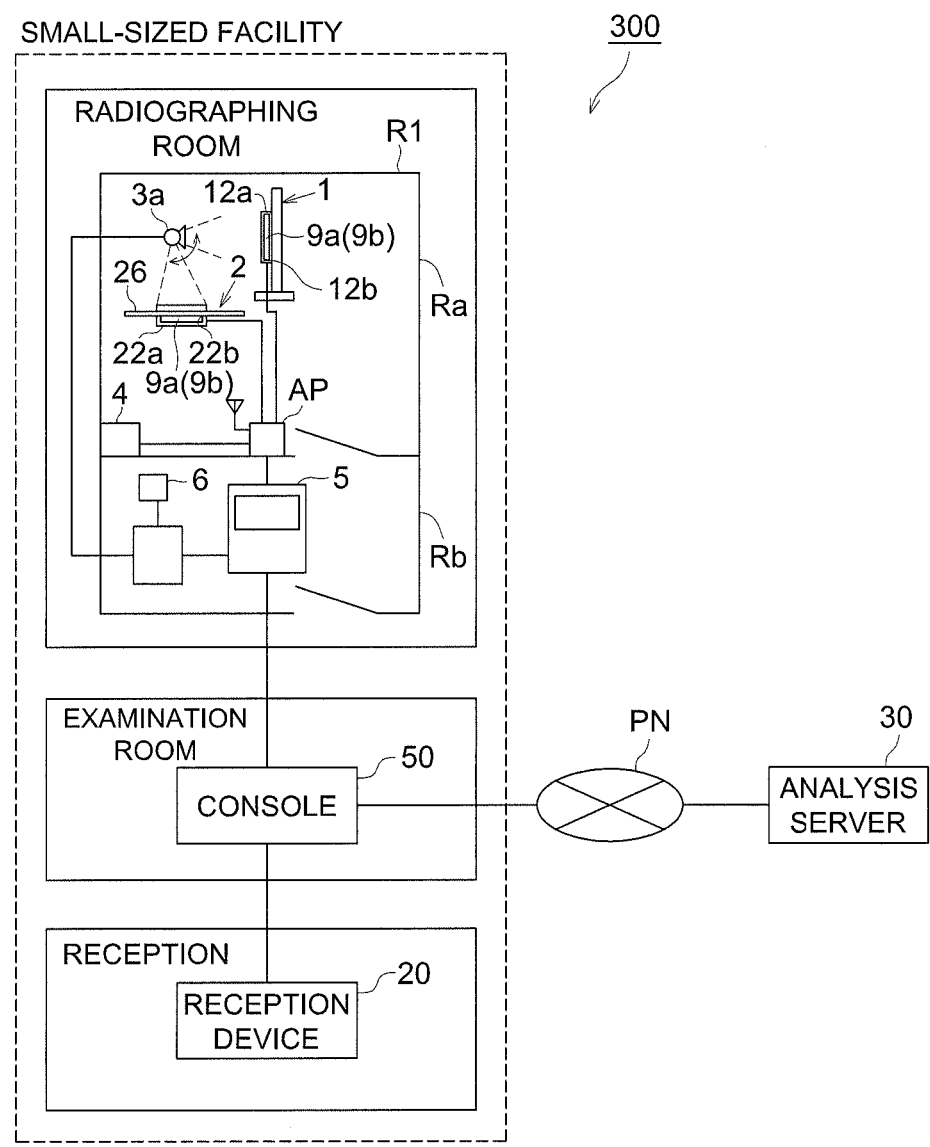
FIG. 17 is a diagram showing the overall structure of the diagnosis support information generation system in a second embodiment.

FIG. 17 illustrates the overall structure of the diagnosis support information generation system 300 in the second embodiment.

The diagnosis support information generation system 300 uses an analysis server 30 an analysis center to analyze the dynamic image radiographed in a small-sized facility such as a practicing doctor' office or clinic, and sends the result of analysis back to the small-sized facility. As described with reference to the first embodiment, the operator to perform the analysis is not required to take care of the pixel size of the FPD or the dynamic range of each pixel, when warping is not needed. Thus, independently of the type of the FPD used in each facility, analysis services can be provided in an open system, as will be described below.

As shown in FIG. 17, a reception device 20 is provided for reception in small-sized facilities, and the examination mom is equipped with a console 50. The radiographing room includes a device (e.g., Bucky's radiographic devices 1 and 2, radiation source 3a, and FPD 9a) in the radiographing room described with reference to the first embodiment. The console 50 is connected with the reception device 20 and Bucky's radiographic device through LAN. Further, the console 50 can be connected with the analysis server 30 through the Internet PN.

The reception device 20 is a computer device for registering the reception of a visiting patient, accounting services and insurance score calculation. When the reception number and patient information (e.g., "Patient ID", "Full name", "Date of birth", "Sex", "Age", "Address", "Telephone number" and "Insurance number") have been inputted, the reception device 20 sends them to the inputted reception number and patient information to the console 50.

The console 50 controls various devices in the radiographing room to perform radiographic operation. It is connected with the analysis server 30 for communication, thereby acquiring and displays the result of analyzing the dynamic image.

Similarly to the case of the console 5 of FIG. 3, the console 50 includes a control section 51, memory section 52, input section 53, display section 54, communication I/F 55, and network communication section 56. These components are connected by a bus 57.

The memory section 52 of the console 50 includes various programs compatible with the console 50. The control section 51 performs various forms of processing including the radiographing/analysis processing B to be described later in conformity to the relevant program. It should be noted that a radiographing management table 521 is not necessary in the console 50. Further, the network communication section 56 can be connected for communication with the external equipment such as an analysis server 30 via the Internet PN, as well as with the devices inside the facilities connected through the switching hub. Otherwise, the structure of the console 50 is the same as that of the console 5, and will not be described to avoid duplication.

The structure of the devices in the radiographing room is the same as that of the first embodiment, and will not be described to avoid duplication.

The analysis server 30 is a server device installed at an external analysis center. The analysis server 30 includes a control section made up of a CPU and others, a memory section storing the analysis program, an input section, a memory section and a communication section. The analysis server 30 performs radiographing/analysis processing B in collaboration with analysis programs stored in the control section and memory section in conformity to the requirements from the console 50. The analysis result is then sent to the console 50. It should be noted that, similarly to the case of the aforementioned WS 8 for analysis, the analysis server 30 does not apply a process of warping. If a process of warping is required, the analysis server 30 must be provided with such information as a pixel size of the FPD of each manufacturer, the dynamic range, of each pixel and radiation dose. Since warping is omitted, it is possible to handle various forms of FPDs supplied by various companies. Further, a substantial reduction of analysis processing time can be achieved.

The following describes the operations of the diagnosis support information generation system 300.

As described above, a visiting patient is provided with a reception number from personnel in charge of reception. The reception number, patient information and others are inputted by the reception device 20. In the control section of the reception device 20, the patient reception number and patient information are inputted from the input section. The inputted information is stored in the memory section and the reception is registered. At the same time, the inputted information (reception list information) is sent to the console 50 by the communication section. In the control section of the console 50, when the reception list information has been received from the reception device 20 by the network communication section 56, the received reception list information is stored in the memory section 52. Further, in response to the operation from the input section 53, a list of the reception list information for the day is displayed on the display section 54.

When the patient assigned with the reception number moves to an examination room, the doctor operates the input section 53 and selects the reception list information of the patient to be examined, from the reception list information displayed on the display section 54. In the console 50, when a reception list has been selected from the reception list information, the diagnosis screen for the patient corresponding to the selected reception list is displayed on the display section 54. The diagnosis screen includes the display column of the radiographed image of the relevant patient and the examination information input column, for example. The doctor gives a medical examination by interview and determines the details of radiographic operation to be performed. If radiographing of a dynamic image and analysis is required as a result of examination by interview, the doctor operates the input section 53 to allow the console 50 to perform the following radiographing/analysis processing B:

The following describes the radiographing/analysis processing B.

Figure 18:
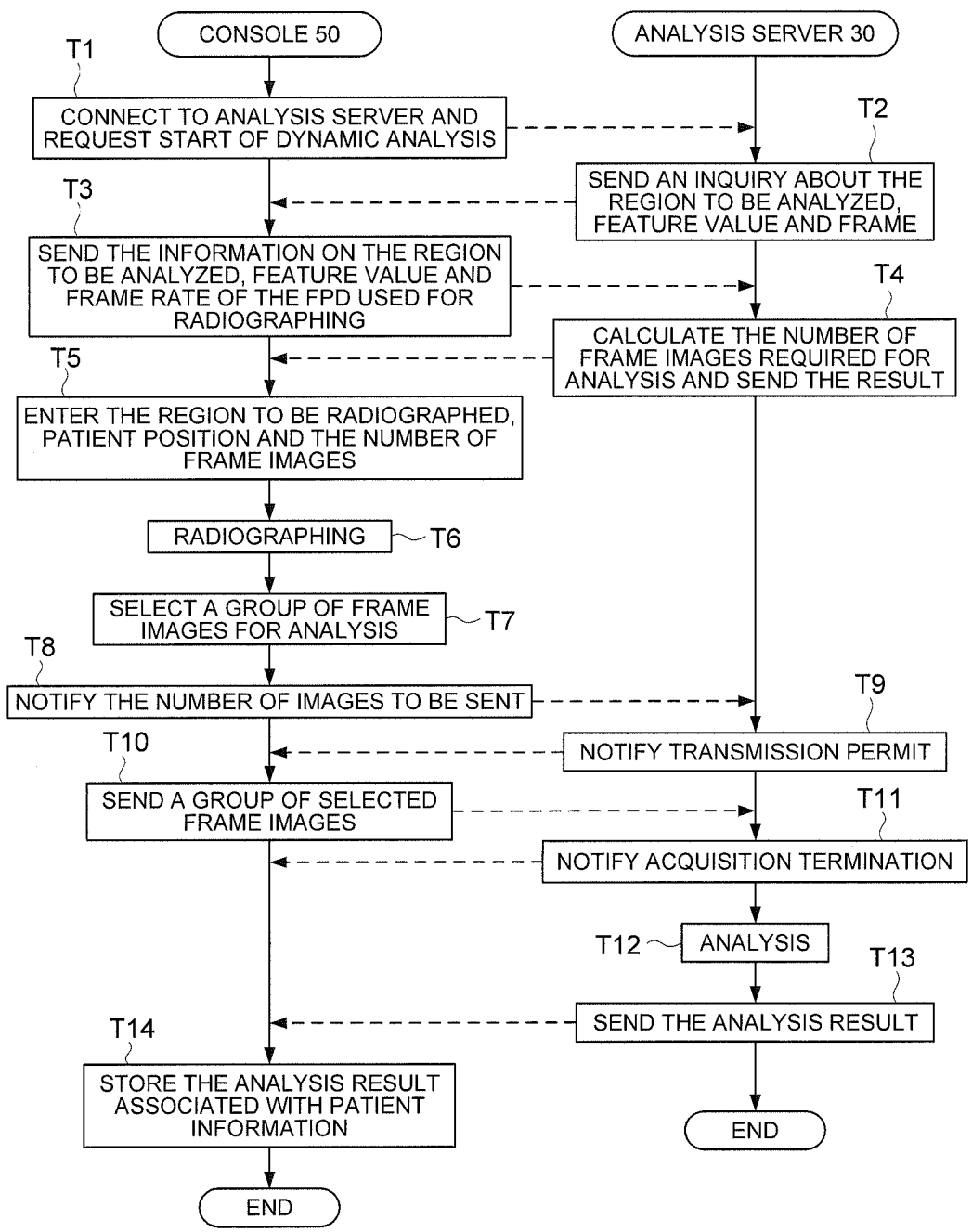
FIG. 18 is a flow diagram showing the operation of the diagnosis support information generation system in the second embodiment.

FIG. 18 shows the flow of the dynamic analysis conducted by the diagnosis support information generation system 300. Radiographing/analysis processing B on the part of the console 50 is executed in collaboration with the programs stored in the control section 51 and memory section 52 of the console 50. Processing on the part of the analysis server 30 is executed in collaboration with the programs stored in the control section and memory section of the analysis server 30.

In the console 50, access to the analysis server 30 is made by the network communication section 56, and a request is issued to start dynamic analysis (Step T1).

In the analysis server 30, upon receipt of the dynamic analysis startup request, an enquiry is sent to the console 50 regarding the region to be analyzed, the feature value, and the frame rate of the FPD to be used (Step T2).

The console 50 acquires information on the region to be analyzed, the feature value (analysis items), and the frame rate of the FPD to be used. This information is sent to the analysis server 30 by network communication section 56 (Step T3). In Step T3, an enquiry from the analysis server 30 is displayed on the display section 54. When the doctor has operated the input section 53 to enter the region to be analyzed, the feature value, and the frame rate of the FPD to be used, the inputted information is sent to the analysis server 30 by the network communication section 56. When the lung field is an object for analysis, feature values are those listed in (1) through (15) described with reference to Step S19 of FIG. 6 in the first embodiment.

In the analysis server 30, when the region to be analyzed, the feature value, and the frame rate has been received from the console 50, the number of frame images required for analysis is calculated and the result is notified to the console 50 (Step T4). The method of calculating the number of frame images required for analysis is the same as described with reference to Step S17 of FIG. 6. To be more specific, the dynamic cycle of the average adult person is stored in the memory section of the analysis server 30 for each region, and the number of frame images required for the analysis is calculated based on the frame rate and dynamic cycle of the region to be analyzed.

When the console 50 has been notified of the number of frame images required for radiographing, notified information such as the number of frame images, radiographed region and patient position is inputted into the input section 53 (Step T5). The process of radiographing is performed in conformity to the inputted information (Step T6). Radiographing is performed approximately in the same way as in Steps S4 through S13 (or S14) of FIG. 6. Here the doctor or radiographer takes the patient into the radiographing room and mounts the FPD 9a on the Bucky's radiographic device (1 or 2) at the position of the patient to be radiographed.

In the console 50, the radiation source 3a and Bucky's radiographic device (1 or 2) is started based on the inputted information on the number of frame images, radiographed region and patient position, and the position and orientation of the radiation source 3a are adjusted. Further, irradiation conditions are set on the radiation source 3a in conformity to the inputted information on the number of frame images, radiographed region and patient position, and image reading conditions are set on the FPD 9a. When analysis is made using the result of radiographing dynamic image, the frame rate is set at 3.75 frames per second or more to ensure the analysis precision that can be used for diagnosis. When the irradiation instruction is inputted from the operation console 6, the radiation source 3a and FPD 9a are placed under the control of the console 50, and radiographing dynamic image is performed. Upon completion of radiographing based on the inputted information on the number of frame images plus some more, the radiographing operation is suspended.

The frame images captured by radiographing are sequentially inputted into the console 50 by the connector 94 of the FPD 9a through the Bucky's radiographic device. The inputted frame image is stored in the memory section 52, and is subjected to thinning processing. Thinning processing includes binning processing and/or simple thinning processing. Regarding the details of thinning processing to be performed, the number of pixels (block size) subjected to binning processing or pixel intervals for simple thinning processing, it is also possible to make such arrangements that the values conforming to the region and feature value of the object to be analyzed received by the analysis server 30, together with the number of frame images, are notified to the console 50 from the analysis server 30 prior to radiographing. The images subjected to thinning-out operation are displayed on the display section 54. Watching the frame image displayed on the display section 54, the radiographer checks positioning or the like. His evaluation on whether an image suited for diagnosis has been captured by radiographing (radiographing: OK) or re-radiographing is necessary (radiographing: NG) is inputted from the input section 53. It is also possible to make such arrangements that each of frame images acquired by radiographing is once stored in the memory section 93 of the FPD 9a, and after completion of all radiographing operations, these frame images are collectively sent to the console 50 of the FPD 9a. If the "radiographing: NG" is inputted from the input section 53, the inputted frame image is deleted from the memory section 52. In this case, re-radiographing is performed. If the decision "radiographing: OK" is inputted by prescribed operations of the input section 53, processing goes to Step T7.

In Step T7 of FIG. 18, the frame image to be used for analysis is selected (Step T7). If the frame images in the number greater than that required for analysis are used for analysis as described above, much time must be spent for data transfer and analysis processing. This is not preferred. To reduce the processing time, the frame images in the number required for analysis have to be selected from among a series of radiographed frame images. In the meantime, the dynamic image is analyzed in conformity to the dynamic cycle or difference of the signal values between adjacent frame images. Thus, to use the dynamic image analysis result as the result for representing the true feature value of a subject, it is necessary to get a series of continuous frame images in the number corresponding to one or more dynamic cycle of the subject. Thus, in Step T7, a selection screen 541 is provided as a GUI (Graphical User Interface) for allowing the operator to correctly select continuous frame images in the number required for analysis. To put it more specifically, selection of discontinuous images for each frame or selection of below one cycle is prevented by using the selection frame 541a for selection. The selection screen 541 and the operations thereof are the same as that described with reference to the first embodiment and will not described to avoid duplication.

When the group of frame images used for analysis has been selected, the number of images to be sent is notified to the analysis server 30 by the network communication section 56 (Step T8). When the analysis server 30 is enabled to receive the notified number of pieces of image data, a transmission permit notice is sent to the console 50 (Step T9). In the console 50, when the transmission permit notice has been received from the analysis server 30 by the network communication section 56, the thin-out data of the selected group of frame images is sent to the analysis server 30 (Step T10). In this case, the information such as patient information and the number indicating the order of radiographing operations is added to the thin-out data of the selection group of a series of frame images (e.g., written into the header area of the image data in the file format of the DICO Mufti-format).

In the analysis server 30, upon completion of acquiring the images in the number notified from the console 50, the acquisition completion notice is sent to the console 50 (Step T11). Then the process of analysis is executed (Step T11). In the process of analysis, non-use of the warping process is preferred from the viewpoint of reducing the processing time, as described with reference to the first embodiment. An example of analysis processing is the same as that described with reference to Step S19 of FIG. 6, and will not be described to avoid duplication.

Upon completion of analysis, the analysis result data is sent to the console 50. In the console 50, analysis result data is associated with the information on the patient selected as a subject of diagnosis, and is stored in the memory section 52. Then the radiographing/analysis processing B terminates.

According to the diagnosis support information generation system 300 of the second embodiment, the frame image subsequent to thinning processing is sent to the analysis server 30. As compared to the case of sending the entire radiographed image data, the communication time is reduced, and the image data required for analysis is sent to the analysis server 30 in a short time. The frame image created by the console 5 for confirmation of positioning can be re-used as the thinned-out frame image. This eliminates the need of taking the trouble of performing the thinning processing again. Further; in the analysis server 30, thin-out data is used for analysis without warping. As compared to the case of performing analysis using the entire image data by application of the process of warping, this procedure provides a substantial reduction of analysis processing time and renders a highly responsive analysis service. Further, if the ROI area is extracted from the frame image sent from the console 50, and only the image data of the extracted ROI area is sent to the analysis server 30, then the communication time and processing time in the analysis server 30 are reduced, and earlier acquisition of the analysis result is ensured.

As described above, according to the diagnosis support information generation system, the WS 8 for analysis ensures that the pixels indicating the output of the detecting element at the same position of the FPD 9a are associated among a plurality of frame images without warping among frame images, and calculates the feature value of a moving subject.

Accordingly, in the analysis of a dynamic image, processing time can be reduced by the time required for warping in the conventional method. This signifies a substantial reduction of the analysis time. This also enables dynamic images to be analyzed without the need of using such hardware as a high-capacity memory and high-speed CPU that would be required for warping.

The console 5 applies thinning processing to reduce the number of pixels in a plurality of frame images captured by radiographing, and sends the result to the WS 8 for analysis. The WS 8 for analysis calculates the feature value using the frame images wherein the number of pixels has been reduced by thinning processing. This means a substantial reduction in the amount of data used for computation and the processing time required for analysis.

In thinning processing, binning processing is preferably applied in such a way that each frame image is divided into a plurality of pixel blocks, and a representative value for pixel signal values is calculated for each relevant pixel block. Then the relevant representative value is replaced by the pixel signal value inside the pixel block, whereby the number of pixels in each frame image is reduced. Since a plurality of frame images subjected to the binning processing are used for analysis, a substantial reduction of processing time can be achieved. Further, fluctuation of the pixels of the FPD is reduced.

Also, since each frame image is divided into a plurality of pixel blocks in the size conforming to the region to be analyzed, it is possible to get the analysis result characterized by the level of precision required for the diagnosis of that region.

Further, since each frame image is divided into a plurality of pixel blocks in the size conforming to the feature value calculated by the WS 8 for analysis, the feature value characterized by the level of precision required for the diagnosis of that region can be obtained as the analysis result.

When the feature value for the ventilation of the lung field is to be calculated, each frame image is divided into pixel blocks of a square of 2 mm×2 mm through 5×5 mm. This makes it possible to calculate the ventilation feature value characterized by the level of precision required for the diagnosis to be performed in a short processing time.

The aforementioned embodiment discloses only a preferable example of the present invention, without the present invention being restricted thereto. For example, in the above description of the embodiment, thinning processing is applied in the console 5 and console 50. For example, it is also possible to make such arrangements that binning processing or simple thinning processing is performed on the radiographing device (FPD 9a in this embodiment) wherein dynamic images are radiographed, and the processed frame image is sent to the console 5, as disclosed in the Official Gazette of Japanese Patent Laid-Open No. 4,546,174. This procedure is more preferred because the image data transfer time between the FPD and console can also be reduced.

In the above description of the first embodiment, the WS 8 for analysis is installed separately from the console 5. It is also possible to make such arrangements that analysis is performed by the console 5 provided with an analysis program. This structure eliminates the time for sending the image data from the console 5 to the WS 8 for analysis and prevents a processing delay from being caused by the analysis made by another console 5.

In the above description, an example of using the nonvolatile memory such as a HDD or semiconductor is disclosed to show a computer readable medium for the program of the present invention. However, the present invention is not restricted thereto. A portable recording medium such as a CD-ROM can also be used as a computer readable medium. Further, a carrier wave can also be used as a medium for supplying the data of the program for the present invention through a communication line.

Further, the detailed structure and operations of the devices constituting the diagnosis support information generation system can be embodied in many variations with appropriate modification or addition, without departing from the technological spirit and scope of the invention claimed.

According to the present embodiment, processing time in the analysis of dynamic images can be reduced without using such hardware as a high-capacity memory or high-speed CPU.

What is claimed is:

1. A dynamic diagnosis support information generation system for a chest which is in respiratory movement comprising:

a radiation generator capable of irradiating a radiation;

a radiation detector comprising a plurality of detecting elements arranged in two dimension, the radiation detector being configured to detect the radiation irradiated from the radiation generator at each of the plurality of detecting elements and generate frame images successively; and an analysis section configured to calculate and output a respective feature value for each of a ventilation and a blood flow of the chest based on a plurality of the frame images generated by radiographing a subject using the radiation generator and the radiation detector which produces a dynamic image of the subject, the dynamic image representing a state of a movement of the subject, wherein for each calculation of each respective feature value, the analysis section is configured to:

apply a filtering in the direction of a time axis for each output signal of the plurality of detecting elements representing both of the ventilation and the blood flow in order to obtain a filtered output signal for each detecting element corresponding to respective pixels of the plurality of the frame images, and wherein the filtered output signal represents only one among the ventilation and the blood flow corresponding to the respective feature value being calculated, and calculate the respective feature value by correlating mutually each filtered output signal for a respective pixel position among the plurality of the frame images corresponding to a same position in the radiation detector, wherein in calculating the feature value for the blood flow, a high-pass filter in the direction of the time axis is applied as the filtering, and wherein in calculating the feature value for the ventilation, a low pass filter in the direction of the time axis is applied as the filtering.

2. The dynamic diagnosis support information generation system described in claim 1, wherein a frame rate for the successive frame images is greater than 7.5 frames per second.

3. The dynamic diagnosis support information generation system described in claim 1, wherein the analysis section correlates some pixels of the radiation detector into a block and calculates a value representing the block by using the filtered output signals of the pixels in the block and correlates mutually each value among the plurality of the frame images at a same position in the radiation detector.

4. The dynamic diagnosis support information generation system described in claim 3, wherein a size of each block is not greater than 5 mm.

5. The dynamic diagnosis support information generation system described in claim 4, wherein a frame rate for the successive frame images is greater than 7.5 frames per second.

* * * * *